US010424469B2

(12) United States Patent
Janka

(10) Patent No.: US 10,424,469 B2
(45) Date of Patent: Sep. 24, 2019

(54) APPARATUS AND METHOD FOR PARTICLE MEASUREMENT

(71) Applicant: Pegasor Oy, Tampere (FI)

(72) Inventor: Kauko Janka, Tampere (FI)

(73) Assignee: Pegasor Oy, Tampere (FI)

( * ) Notice: Subject to any disclaimer, the term of this patent is extended or adjusted under 35 U.S.C. 154(b) by 0 days.

(21) Appl. No.: 15/772,774

(22) PCT Filed: Nov. 2, 2016

(86) PCT No.: PCT/FI2016/050773

§ 371 (c)(1),
(2) Date: May 1, 2018

(87) PCT Pub. No.: WO2017/077191

PCT Pub. Date: May 11, 2017

(65) Prior Publication Data

US 2018/0342380 A1 Nov. 29, 2018

(30) Foreign Application Priority Data

Nov. 2, 2015 (FI) .................................... 20155787
Nov. 2, 2015 (FI) .................................... 20155788
(Continued)

(51) Int. Cl.
*G01N 15/06* (2006.01)
*G01N 1/22* (2006.01)
(Continued)

(52) U.S. Cl.
CPC ........ *H01J 49/0027* (2013.01); *G01N 1/2273* (2013.01); *G01N 1/38* (2013.01);
(Continued)

(58) Field of Classification Search
CPC ..... H01J 49/0027; G01N 1/2273; G01N 1/38; G01N 15/0656; G01N 1/2211;
(Continued)

(56) References Cited

U.S. PATENT DOCUMENTS 2,595,376 A 5/1952 Zachariassen
3,413,545 A 11/1968 Whitby
(Continued)

FOREIGN PATENT DOCUMENTS

CN 204405387 6/2015
JP S62116232 5/1987
(Continued)

*Primary Examiner* — Nicole M Ippolito
(74) *Attorney, Agent, or Firm* — Leason Ellis LLP

(57) ABSTRACT

The present invention relates to an apparatus (1) for particle measurement. The apparatus (1) comprising a mixing chamber (16) having a sample inlet (14), an ionized gas outlet (12) for feeding ionized clean gas into the mixing chamber (16), and a mixing chamber outlet (18) for discharging mixed sample aerosol formed in the mixing chamber (16). The apparatus further comprises a sample channel (34) connected to the sample inlet (14) and extending in a first supply direction, a sample supply connection (50) arranged to supply sample aerosol to the sample channel (34) and a sample supply channel (52) connected to the sample supply connection (50) in a second supply direction transverse to the first supply direction. The sample supply connection (50) is arranged to supply the sample aerosol from the sample supply channel (52) to the sample channel (34) as a swirling sample aerosol flow.

12 Claims, 9 Drawing Sheets

(30) Foreign Application Priority Data

Nov. 2, 2015 (FI) ..................................... 20155789
Nov. 2, 2015 (FI) ..................................... 20155790

(51) Int. Cl.

| | |
|---|---|
| ***H01J 49/00*** | (2006.01) |
| ***H01J 49/14*** | (2006.01) |
| ***G01N 1/38*** | (2006.01) |
| *G01N 15/00* | (2006.01) |

(52) U.S. Cl.
CPC ....... *G01N 15/0656* (2013.01); *G01N 1/2211* (2013.01); *G01N 2001/2223* (2013.01); *G01N 2001/387* (2013.01); *G01N 2015/0038* (2013.01); *G01N 2015/0046* (2013.01)

(58) Field of Classification Search
CPC ..... G01N 2001/2223; G01N 2001/387; G01N 2015/0038; G01N 2015/0046
USPC ..................... 250/281, 282, 283, 288, 423 R
See application file for complete search history.

(56) References Cited

U.S. PATENT DOCUMENTS 5,723,861 A 3/1998 Carnahan et al.
9,533,063 B1 * 1/2017 Savage .................. A01N 45/00
2004/0182133 A1 9/2004 Staphanos et al.
2006/0061762 A1 * 3/2006 Dwight .................. B82Y 30/00 356/301
2006/0284077 A1 12/2006 Fissan et al.
2007/0029477 A1 2/2007 Miller et al.
2008/0264047 A1 * 10/2008 Griffiths ................ B05B 7/0892 60/299
2011/0024615 A1 * 2/2011 Tanner ................... G01N 15/10 250/282
2011/0050243 A1 3/2011 Tikkanen
2014/0069169 A1 * 3/2014 Janka .................. G01N 1/2252 73/28.02
2014/0076027 A1 3/2014 Nicholson
2014/0339415 A1 11/2014 Caldow et al.

FOREIGN PATENT DOCUMENTS

JP 2006349397 12/2006
WO WO 200122049 3/2001
WO WO 2005059539 6/2005
WO WO 2006/127803 11/2006
WO WO 2012/062964 5/2012
WO WO 2013/132154 9/2013

* cited by examiner

APPARATUS AND METHOD FOR PARTICLE MEASUREMENT

CROSS-REFERENCE TO RELATED PATENT APPLICATIONS

This application is a U.S. National Phase Application under 35 U.S.C. § 371 of International Patent Application No. PCT/FI2016/050773, filed Nov. 2, 2016, which claims the priority of Finnish Application No. 20155787, filed Nov. 2, 2015, Finnish Application No. 20155788, filed Nov. 2, 2015, Finnish Application No. 20155789, filed Nov. 2, 2015, and Finnish Application No. 20155790, filed Nov. 2, 2015, each of which is incorporated by reference as if expressly set forth in its entirety herein.

FIELD OF THE INVENTION

The present invention relates to an apparatus for particle measurement and more particularly to an apparatus according to the preamble of claim 1. The present invention also relates to a method for measuring particles with a particle measurement apparatus and more particularly to a method according to the preamble of claim 15.

BACKGROUND OF THE INVENTION

Fine particles having diameter between 1 nm and 10 μm may be present in inside air of residential building and rooms, office premises and also in industrial buildings as well as in outdoor air and open-air. These fine particles may be formed for example in different kind of combustion processes, industrial processes and also in natural sources. For various reasons these fine particles are measured. The fine particle measurements may be conducted because of their potential health effects and also for monitoring operation of combustion or industrial processes, such as operation of combustion engines, especially diesel engines. The fine particles are also measured in ventilation systems for monitoring air quality. Another reason for monitoring fine particles is the increasing use and production of nanosized particles in industrial processes. The above reasons generate a need for reliable fine particle measurement apparatuses and methods.

Prior art methods and apparatuses for measuring particles comprise measuring fine particles electrically utilizing electrical charging of the fine particles.

In a prior art apparatus clean, essentially particle free, gas is supplied into the apparatus. The clean gas is further ionized before and during supplying it into the apparatus. The prior art apparatus may comprise a corona charger connected to corona voltage source for ionizing the clean gas. The apparatus further comprises sample inlet via which particle containing aerosol sample is supplied into the apparatus. Inside the apparatus the ionized clean gas flow and the particle containing sample aerosol flow are brought into contact with each other and mixed such that a mixed sample aerosol flow is generated. The ionized clean gas electrically charges the particles of the sample aerosol flow by diffusion charging upon contact and mixing of the ionized clean gas and the particle containing sample aerosol flow.

Free ions, meaning ions not attached to particle, may be removed from the mixed sample aerosol flow using ion trap. The ion trap may be an ion trap electrode connected to an ion trap voltage source providing collection voltage for removing the free ions from the mixed sample aerosol flow. The ion trap voltage is high enough to deposit the free ions, but due to the lower mobility charged particles are not deposited.

The mixed sample aerosol flow comprising the electrically charged particles them flows to a filter unit in which the electrically charged particles are collected by a filter. The particle measurement is carried out by measuring the electrical current in the filter generated by the collected electrically charged particles for example with an electrometer. Downstream of the filter unit is arranged a pump or other suction device for providing the clean gas flow and the sample aerosol flow through apparatus.

In many applications the apparatus for particle measurement has to be located in small spaces. Therefore size of the apparatus should be as small as possible for efficient utilization of space. However, decreasing the dimensions of the apparatus may reduce quality of the measurements as the flow dynamics of the sample aerosol are compromised by the decreased dimension. Therefore, for the prior art apparatuses for particles measurement the balance between the dimensions and the measurement quality are a compromise. Small dimensions deteriorate measurement quality and large dimensions cause inefficient space utilization.

BRIEF DESCRIPTION OF THE INVENTION

An object of the present invention is thus to provide a particle measurement apparatus so as to overcome or at least alleviate the above disadvantages. The objects of the present invention are achieved by an apparatus which is characterized by what is stated in the characterizing portion of claim 1. The objects of the present invention are further achieved by a method which is characterized by what is stated in the characterizing portion of claim 15.

The preferred embodiments of the invention are disclosed in the dependent claims.

The present invention is based on the idea of providing an apparatus for particle measurement, the apparatus comprising a sample inlet provided to the mixing chamber for feeding sample aerosol into the mixing chamber, a ionized gas outlet for feeding ionized clean gas into the mixing chamber, and a mixing chamber outlet for discharging mixed sample aerosol formed in the mixing chamber by mixing ionized clean gas and sample aerosol, said mixed sample aerosol comprising electrically charged particles generated by the ionized clean gas. The apparatus further comprises a sample channel connected to the sample inlet for supplying sample aerosol into the mixing chamber via the sample inlet, the sample channel extending in a first supply direction, a sample supply connection arranged to supply sample aerosol to the sample channel and a sample supply channel connected to the sample supply connection in a second supply direction transverse to the first supply direction, the sample supply channel being arranged to supply sample aerosol to the sample channel via the sample supply connection. The sample channel, sample supply connection and the sample supply channel together form a sample supply arrangement for supplying sample aerosol to the mixing chamber.

The apparatus further comprises an ion trap for removing free ions not attached to particles from the mixed sample aerosol and an electrical measurement element arranged to measure electrical current carried by the electrically charged particles.

The sample supply connection being arranged to supply the sample aerosol from the sample supply channel to the sample channel as a swirling sample aerosol flow. The sample supply connection is a connection between the sample supply channel and the sample channel or it is provided between the sample supply channel and the sample channel.

In one embodiment of the present invention sample supply connection is arranged to supply the sample aerosol from the sample supply channel to the sample supply connection tangentially in relation to the first supply direction for proving the swirling sample aerosol flow. This may be achieved by providing the sample supply connection as a tangential connection of the sample supply channel to the sample channel in relation to the first supply direction for providing the swirling aerosol flow around the first central axis along the sample channel. Alternatively the sample channel has a first central axis extending in the first supply direction and circular or elliptical cross-section provided by sample channel side wall, and the sample supply connection is a tangential connection of the sample supply channel to the sample channel side wall in relation to the first central axis for providing the swirling aerosol flow around the first central axis along the sample channel. The second supply direction of the sample supply channel may be transverse to the first supply direction or inclined to the first supply direction or perpendicular to the first supply direction.

In an alternative embodiment of the apparatus for particle measurement according to the present invention the sample supply connection comprises a sample supply chamber arranged between the sample supply channel and the sample channel and arranged to supply the sample aerosol from the sample supply channel to the sample supply chamber tangentially in relation to the first supply direction for proving the swirling sample aerosol flow along the sample channel.

In one embodiment the sample supply chamber has a second central axis extending the first supply direction, the sample supply chamber being arranged to provide the swirling sample aerosol flow around the second central axis and to supply the sample aerosol to the sample channel. The sample supply chamber may be a tubular or cylindrical sample supply chamber having the second central axis extending in the first supply direction and a circular or elliptical cross-section, or circular or elliptical sample supply chamber side wall, the swirling aerosol flow being arranged to flow around the second central axis as swirling sample aerosol flow.

In one embodiment the sample supply channel is connected tangentially to the sample supply chamber for supplying the sample aerosol to the sample supply chamber tangentially, or alternatively the sample supply channel is connected tangentially to the circular or elliptical sample supply chamber side wall of the sample supply chamber for supplying the sample aerosol to the sample supply chamber tangentially. Therefore the sample supply channel is be connected to the sample supply chamber in the second supply direction, the second supply direction may be transverse to the first supply direction, or inclined to the first supply direction, or perpendicular to the first supply direction.

In operating stage of the apparatus the first supply direction may be vertical direction and the second supply direction may be horizontal direction, or alternatively the first supply direction may be horizontal direction and the second supply direction may be vertical direction.

In some embodiment the sample supply connection or the sample supply chamber may comprise one or more guide vanes provided inside or to inner walls of the sample supply or sample supply chamber for providing the swirling sample aerosol flow to the sample channel.

The sample supply chamber may be a separate chamber provided between the sample supply channel and the sample channel, or that the upper end of the sample channel forms the sample supply chamber.

The apparatus may further comprise an ionization chamber, a filter unit, a pump and a discharge channel connected to the pump, as disclosed in the detailed description of the invention. The electrical measurement element may be connected to the filter unit for measure electrical current carried by the electrically charged particles and deposited to the filter unit The apparatus may further comprise a preliminary separation device connected to the sample supply channel upstream of the sample supply. The preliminary separation device may be arranged adjacent the mixing chamber.

The present invention also relates to a method for particle measurement with an apparatus for particles measurement. The method comprises:

feeding sample aerosol containing particles into the mixing chamber along sample channel and via a sample inlet provided to a mixing chamber, the sample channel extending in a first supply direction;

feeding ionized clean gas into the mixing chamber via ionized gas outlet;

mixing ionized clean gas and sample aerosol in the mixing chamber for electrically charging particles of the sample aerosol and providing mixed sample aerosol comprising electrically charged particles generated by the ionized clean gas;

removing free ions not attached to particles from the mixed sample aerosol;

measuring electric current carried by the electrically charged particles;

supplying sample aerosol to the sample channel via a sample supply connection from a second supply direction transverse to the first supply direction such that a swirling sample aerosol flow is generated to the sample channel in relation to the first supply direction.

In one embodiment of the present invention the method comprises supplying the sample aerosol tangentially to the sample supply connection from the second supply direction transverse to the first supply direction for providing the swirling sample aerosol flow to the sample channel in relation to the first supply direction.

The sample aerosol has to be supplied into the apparatus and mixing chamber in homogenous and equalized manner in order to provide reliable measurement results. Thus the sample aerosol flow has to be homogenized and equalized in the first supplied direction along the sample channel. Supplying the sample aerosol to the mixing chamber requires usually a long sample channel for equalizing or homogenizing the sample aerosol flow in the first supply direction, meaning in the direction of the first central axis of the sample channel. In other words the sample aerosol has to be homogenized in the first supply direction which is the direction in which the sample aerosol is fed into the apparatus and the mixing chamber. Homogenizing and equalizing the sample aerosol therefore requires long sample channel and also adequate flow tome the first supply direction. However, the long sample channel increases the dimensions of the apparatus, but if the sample channel is shortened the measurement quality is decreased as the sample aerosol enters the apparatus and mixing chamber unequalized and unhomogenized manner.

In the present invention the prior art disadvantages are solved or at least alleviated by providing a sample supply connection via which the sample aerosol is supplied to the sample channel as a swirling sample aerosol flow. The swirling sample aerosol flow means that the sample aerosol flows in rotating manner along the sample channel to the sample inlet. The swirling or rotating flow in the sample channel is achieved by providing a sample supply connection arranged to supply the sample aerosol from the sample supply channel to the sample channel as a swirling sample aerosol flow. The sample supply connection is provided as a tangential connection of the sample supply channel to the sample channel in relation to the first supply direction for providing the swirling aerosol flow around the first central axis along the sample channel. The sample supply connection comprises may also comprise the sample supply chamber arranged between the sample supply channel and the sample channel and arranged to supply the sample aerosol from the sample supply channel to the sample supply chamber tangentially in relation to the first supply direction for proving the swirling sample aerosol flow.

An advantage of the apparatus and method according to the present invention is that the swirling or rotating sample aerosol flow in the sample channel homogenizes and equalizes the sample aerosol in the sample channel. Thus the swirling or rotating sample aerosol flow travels in homogenous manner along sample channel when viewed in radially. Accordingly, the homogenizing effect of the swirling or rotating sample aerosol flow enables using shorter sample channel for achieving necessary homogenization and equalization of the sample aerosol without compromising the quality of the measurement results. Thus the dimensions of the apparats may be decreased.

BRIEF DESCRIPTION OF THE DRAWINGS

In the following the invention will be described in greater detail by means of preferred embodiments with reference to the accompanying drawings, in which.

DETAILED DESCRIPTION OF THE INVENTION

Figure 1:
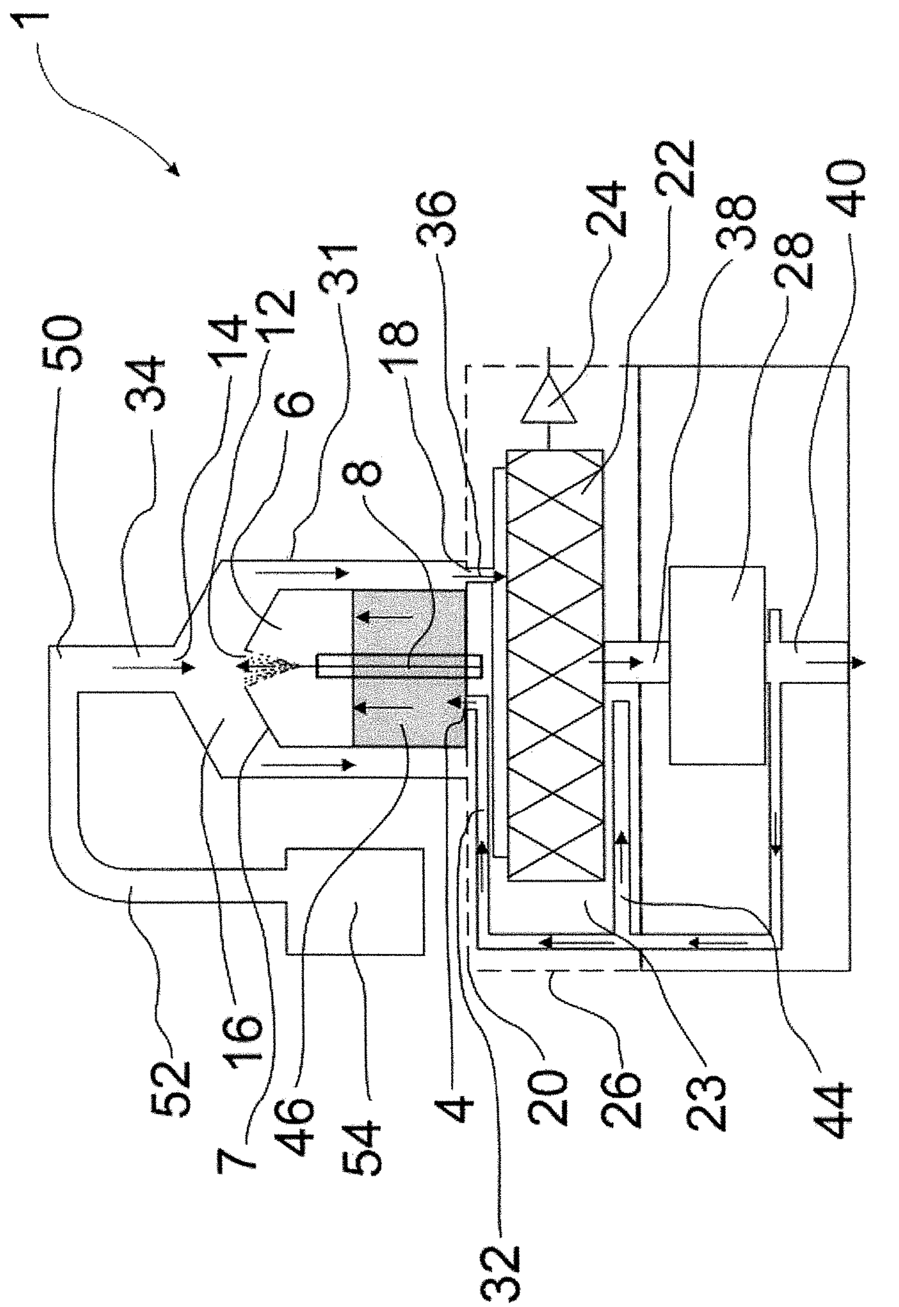
FIG. 1 shows one embodiment of an apparatus for particle measurement according to the present invention.

FIG. 1 shows one embodiment of an apparatus 1 for particle measurement according to the present invention.

The apparatus 1 of FIG. 1 comprises an ionization chamber 6 for supplying clean ionized gas to the apparatus. The clean gas in the context of this application means essentially particle free gas. The ionization chamber 6 comprises a clean gas inlet 4 via which the clean gas is supplied into the ionization chamber 6. The ionization chamber is further provided with electrical charging element 8 which is arranged to electrically charge the clean gas during or after supplying the clean gas via the clean gas inlet 4 into the apparatus 1 and the ionization chamber 6. The electrical charging element 8 is connected to charging voltage source 10 for providing charging voltage to the electrical charging element 8. The charging voltage source 10 may be any kind voltage source, such as high voltage source. The electrical charging element 8 electrically charges the clean gas as it passes the electrical charging element 8. Thus the ionization chamber 6 provides an ionized clean gas flow into the apparatus 1.

In one embodiment of the apparatus 1 of FIG. 1 the electrical charging element 8 is a corona electrode and the charging voltage source 10 is a corona voltage source.

The clean gas is supplied via clean gas channel 32 into the ionization chamber 6 and the clean gas enters the ionization chamber 6 from the clean gas inlet 4 provided to the ionization chamber 6. The electrical charging element 8 is provided into the ionization chamber 6 such that the clean gas flow passes the electrical charging element 8 as it flows through the ionization chamber 6. The electrical charging element 8, or corona electrode, may be arranged for example to extend inside the charging chamber 6, as shown in FIG. 1. In one embodiment the electrical charging element 8 may be arranged to extend in the centre of the ionization chamber 6. The electrical charging element 8 may be a rod or wire which is electrically connected to the charging voltage source. Accordingly, the ionization of the clean gas is carried out in the ionization chamber 6. The ionization chamber 6 further comprises an ionized gas outlet 12 via which the ionized clean gas is discharged from the ionization chamber 6.

The ionization chamber 6 comprises chamber walls 7 defining the ionization chamber 6. The clean gas inlet 4 and the ionized gas outlet 12 may be arranged such that the clean gas flows through the ionization chamber 6 passing the electrical charging element 8 between the clean gas inlet 4 and the ionized gas outlet 12. In one embodiment the clean gas inlet 4 and the ionized gas outlet 12 are arranged opposite each other in the ionization chamber 6 and the electrical charging element 8 is arranged between the clean gas inlet 4 and the ionized gas outlet 12, as shown in FIG. 1. Thus the ionization chamber 6 is provided as flow-through chamber in which the clean gas flows through the ionization chamber 6 from the clean gas inlet 4 directly to the ionized gas outlet 12. In the embodiment of the apparatus of FIG. 1 the ionization chamber walls 7 are arranged converge towards the ionized gas outlet 12. Thus the ionization chamber 6 tapers towards the ionized gas outlet 12. The ionization chamber 6 therefore may be arranged to taper from the clean gas outlet 4 towards the ionized gas outlet 12 for providing ionized clean gas flow from the ionization chamber 6.

In an alternative embodiment the clean gas inlet 4 and the ionized gas outlet 12 are arranged to the ionization chamber wall 7 transversely or perpendicularly in relation to each other.

As shown in FIG. 1, the ionization chamber 6 is further provided with a clean gas filter 46 arranged inside the ionization chamber 6. The clean gas filter 46 may be HEPA filter or a carbon filter. The clean gas filter 46 is provide downstream of the clean gas inlet inside the ionization chamber 6 such that the clean gas flows though the clean gas filter 46 in the ionization chamber for removing particulate matter from the clean gas. It should be noted that he clean gas filter 46 may also be omitted.

Alternatively the clean gas filter may be arranged upstream of the clean gas inlet 4 and to the clean gas channel 32.

In an alternative embodiment the ionization chamber 6 may be omitted. In this case the electrical charging element 8 may be provided to the clean gas channel 32 such that the clean gas is ionized inside the clean gas channel 32 or at the clean gas inlet 4. In this embodiment ionized clean gas in supplied via the clean gas inlet 4. In this case also the clean gas filter 46 may be arranged to the clean gas channel 32 upstream of the electrical charging element 8.

The apparatus 1 further comprises a sample inlet 14 via which sample aerosol flow is supplied into the apparatus 1. The sample aerosol flow is supplied into the apparatus from a space comprising aerosol to be measured with the particle measurement apparatus 1. The space may be a habitable space, industrial space, process chamber, ventilation system, combustion system, exhaust conduit or any other space comprising particle containing aerosol.

The apparatus also comprises a sample channel 34 via which the sample aerosol is supplied to the sample inlet 14.

The apparatus may also comprise sample supply channel 52 with which sample aerosol is transported from the space comprising the aerosol to be measured to the sample channel 34. The sample supply channel 52 is connected to the sample channel 34 with sample supply connection 50 for supplying the sample aerosol from the sample supply channel 52 to the sample channel 34.

As shown in FIG. 1, the apparatus may further comprises a preliminary separation device 54 connected to the sample supply channel 52 upstream of the sample supply connection 50. The preliminary separation device may be cyclone or filter for removing larger particles from the sample aerosol. The preliminary separation device 54 is arranged adjacent the mixing chamber 16 and ionization chamber for minimizing the height of the apparatus. The preliminary separation device 54 may also be replaced with any other kind of process device.

The apparatus 1 comprises a mixing chamber 16 in which the ionized clean gas and the particle containing sample aerosol meet each other and are mixed with each other for providing a mixed sample aerosol. The mixing chamber 16 is defined by mixing chamber walls 31. The ionized clean gas enters the mixing chamber 16 from the ionized gas outlet 12 and the sample aerosol enters the mixing chamber from the sample inlet 14. In the mixing chamber 16 the ionized clean gas and the sample aerosol collide and mix with each other such that the ionized clean gas electrically charges the particles of the sample aerosol providing a mixed sample aerosol comprising electrically charged particles. The charging of the particles occurs mainly by diffusion charging such that ions in the ionized clean gas are attached to the particles and the particles become electrically charged.

In the embodiment of FIG. 1 the ionized clean gas enters the mixing chamber 16 from the ionized gas outlet 12 and the sample aerosol enters the mixing chamber 16 from the sample inlet 14 opposite the ionized gas outlet 12 and ionized clean gas is generated such that the ionized clean gas and the sample aerosol collide to each other and becomes mixed. In the embodiment of FIG. 1 the ionized gas outlet 12 is arranged towards and opposite the sample inlet 14 and the ionized clean gas enters the mixing chamber 16 in a third flow direction. The sample inlet 14 is arranged towards and opposite the ionized gas outlet 12 and the sample aerosol enters the mixing chamber 16 in a first flow direction opposite the third flow direction of the ionized clean gas such that the ionized clean gas and the sample aerosol collide directly against each other and are mixed inside the mixing chamber 16 for electrically charging the particles of the sample aerosol. In other words, arranging the ionized gas outlet 12 and the sample inlet 14 opposite each other provides counter current flow of the ionized clean gas and the sample aerosol inside the mixing chamber 16. Thus the ionized clean gas and the sample aerosol may collide directly against each other in a collision angle of substantially 180 degrees.

As shown in FIG. 1, the ionization chamber 6 is defined with the ionization chamber walls 7 and provided inside the mixing chamber 16. Thus the ionization chamber 6 is within the mixing chamber 16 and separated with the ionization chamber walls 7. The mixing chamber 16 and the mixing chamber walls 31 surround the ionization chamber 6. Therefore the ionization chamber 6 is nested inside the mixing chamber 16. There is a gap between the ionization chamber walls 7 and the mixing chamber walls 31, as shown in FIG. 1, for providing a flow path for the mixed sample aerosol flow comprising electrically charged particles.

In an alternative embodiment the ionization chamber may be provided outside of the mixing chamber 16 and the ionized clean gas in transported into the mixing chamber 16 from outside of the mixing chamber 16. In a yet alternative embodiment the ionization chamber 6 is provided to or formed by the clean gas channel 32.

According to the above mentioned the ionization chamber 6 is provided in fluid communication with mixing chamber 16 in all embodiments of the apparatus according to the FIG. 1.

The mixing chamber 16 further comprises mixing chamber outlet 18 via which the mixed sample aerosol comprising electrically charged particles is discharged from the mixing chamber 16. The mixed sample aerosol flows from the flow path between the ionization chamber walls 7 and the mixing chamber walls 31 to mixing chamber outlet 18 and discharges from the mixing chamber 16.

In FIG. 1, the sample inlet 14 is provided to a first end or first end wall of the mixing chamber 16 and the mixing chamber outlet 18 is provided to a second end or second end wall of the mixing chamber 16 opposite the sample inlet 14. Therefore, the mixing chamber 16 is provided as flow-through chamber such that the sample aerosol flows through the mixing chamber 16 and directed in the first flow direction towards the mixing chamber outlet 18.

In an alternative embodiment the mixing chamber outlet 18 may be provided to a side wall of the mixing chamber 16 transversely or perpendicularly to the sample inlet 14.

Figure 2:
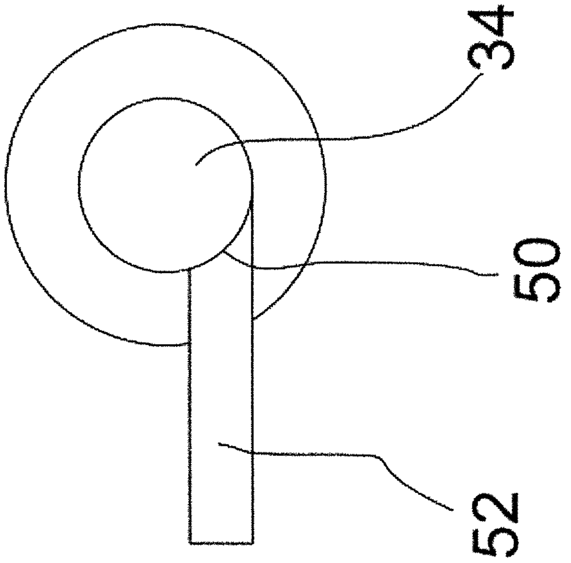
FIG. 2 shows sample supply arrangement according to one embodiment of the present invention.

The mixing chamber 16 is further provided with an ion trap for removing free ions not attached to the particles of the mixed sample aerosol. In the embodiment of FIG. 1 the ion trap is provided by the mixing chamber walls 31. Thus the mixing chamber walls 31 forms the ion trap or an ion trap electrode. As shown in FIG. 2, the charging voltage source 10 is electrically connected to the electrical charging element 8 and to the ionization chamber walls 7. Thus the electrical charging element 8 and the ionization chamber walls 7 are at same electrical potential. The mixing chamber walls 31 are grounded such that the mixing chamber walls 31 form the ion trap electrode for collecting and removing free ions from the mixed sample aerosol as the mixed sample aerosol passes the mixing chamber walls 31 along the gap between the ionization chamber 6 and the mixing chamber 16. Therefore, an electric field is provided between the ionization chamber walls 7 and the mixing chamber walls 31.

The ion trap, or the mixing chamber walls 31, is thus provided as an ion trap electrode or electrodes having opposite polarity than the free ions. Alternative the mixing chamber 16 may be provided with separate electrode or electrodes formed as ion trap electrodes. The separate ion trap electrode may be any kind of electrode, for example such as plate-like electrode or net-like electrode. The ion trap electrode may also be connected to an ion trap voltage source or it may be grounded such that electric field is provided between the electrical charging element 8 and the ionization chamber wall 7, and the ion trap electrode for collecting the free ions not attached to the particles. The ion trap voltage is high enough to deposit the free ions, but due to the lower mobility the electrically charged particles are not deposited to the ion trap electrode.

The ion trap is provided such that the ionized clean gas and the sample aerosol are mixed and the particles electrically charged before the mixed sample aerosol meets the ion trap and is subjected to the ion trap voltage.

In an alternative embodiment the ion trap may be arranged downstream of the mixing chamber 16 and downstream of the mixing chamber outlet 18. Thus in this embodiment the ion trap is separate from the mixing chamber 16.

As shown in FIG. 1, the mixing chamber 16 and the ionization chamber 6 have annular structure such that the ionization chamber 6 is provided inside the mixing chamber 16 and centralized in the mixing chamber 16 such that the gap between the ionization chamber 6 and the mixing chamber 16 is formed. It is important for the operation of the apparatus that the flow of mixed sample aerosol is as homogenous as possible in the ion trap or in the vicinity of the ion trap, meaning in the gap between the ionization chamber 6 and the mixing chamber 16 in FIG. 1. Even small variations in centralization of the ionization chamber 6 inside the mixing chamber 16 causes uneven flow rate such that there where the gap is smaller also the flow rate is smaller and the flow time through the gap longest. This may cause variations in the ion trap function for removing free ions and effects the measurement results. However, the swirling sample aerosol flow in the apparatus and in the mixing chamber 16 and ion trap equalizes differences in flow time and thus decreases required tolerance demands in the apparatus and in the mixing chamber 16 and ionization chamber 6 and their centralization.

The apparatus 1 further comprises a filter unit 20 arranged downstream of the mixing chamber 16, as shown in FIG. 1. The filter unit 20 is arranged in fluid communication with the mixing chamber 16 and downstream of the mixing chamber 16. In the embodiment of FIG. 1, the filter unit 20 is connected to the mixing chamber 16 with filter inlet channel 36 for passing the mixed sample aerosol flow from the mixing chamber 16 to the filter unit 20. Therefore, the mixed sample aerosol flow is passed from the mixing chamber 16 via the mixing chamber outlet 18 and the filter inlet channel 36 to the filter unit 20.

It should be noted that the ion trap is provided upstream or before of the filter unit 20. In FIG. 1, the ion trap is provided inside the mixing chamber 16. In an alternative embodiment the ion trap may also be provided to the filter inlet channel 36 between the mixing chamber 16 and the filter unit 20.

The filter unit 20 comprises a housing 26 inside which a filter 22 is arranged. The housing 20 comprises or is formed as a faraday cage for electrically separating the filter unit 20 from the other parts of the apparatus 1, and especially from the ionization chamber 6, electrical charging element 8, ion trap and the mixing chamber 16. The filter unit 20 further comprises an electrical insulator 23 inside the housing 20. The filter 22 is embedded inside the insulator 23 for further electrically insulating the filter 22 from the other parts of the apparatus 1. The filter 22 may be any kind of conventional filter, such as a membrane filter or some other kind of filter effective to filter particles. The structure of the filter unit 20 is arranged such that the filter 22 may be removed from the filter unit 20 and replaced or changed to a new filter 22.

The electrically charged particles of the mixed sample aerosol are filtered and removed from the mixed sample aerosol in the filter 22. During the filtration with the filter 22 the electrically charged particles are deposited to the filter 22 and accumulate to the filter 22.

As the electrically charged particles are deposited to the filter 22 they generate electrical current to the filter 22. The filter unit 20 therefore further comprises an electrical measurement element 24 connected to the filter 22. The electrical measurement element 24 is arranged to measure the electrical current produced by the electrically charged particles in the filter 22 as they are deposited to the filter 22. The electrical measurement element 24 provides an output signal based on the measurement results of the electrical current measurements from the filter 22. The output signal may be transmitted to a process unit (not shown) for further analysis. The electrical measurement element 24 may comprise an electrometer or the like measuring device.

The ion trap has to be arranged upstream of or before the filter unit 20 such that the free ions present invention mixed sample aerosol do not affect the particle measurement with the electrical measurement element 24 based on the measuring the electrical current carried by the electrically charged particles.

In the filter unit 20 the electrically charged particles are filtered from the mixed sample aerosol and a filtered mixed sample aerosol flow is discharged from the filter unit 20.

Downstream of the filter unit 20 is provided a pump 28 or other kind of suction device. The pump 28 is arranged in fluid communication with the filter unit 20 and arranged downstream of the filter unit 20. The pump 28 is arranged to generate flow of at least sample aerosol, mixed sample aerosol and filtered mixed sample aerosol through the apparatus 1. The pump 28 may also be arranged to generate flow of the clean gas and ionized clean gas into or in the apparatus 1.

The pump 28 is connected to the filter unit 20 with a filter output channel 38 extending between the filter unit 20 and the pump 28 for passing the filtered mixed sample aerosol from the filter unit 20 to the pump 28. The filtered mixed sample aerosol is discharged from the pump 28 and from the apparatus 1 via discharge channel 40. The filtered mixed sample aerosol may be discharged via the discharge channel 40 out of the apparatus 1 to environment or back to the space from where it was taken.

As shown in FIG. 2, the apparatus comprises a flow through structure such that the sample aerosol flows in the second flow direction through the apparatus 1. This enables effective constructions and operation of the apparatus such that the size or height of the apparatus 1 may be minimized. This means the sample inlet 14, filter unit 20 and the pump 28 are arranged in line with each other. In one embodiment the sample inlet 14, mixing chamber 16, filter unit 20 and the pump 28 are all arranged in line with each other. In a yet alternative embodiment the sample inlet 14, mixing chamber 16, ionization chamber 6, filter unit 20, the pump 28 and the discharge channel 40 are all arranged in line with each other.

In this embodiment the clean gas channel 32 extends between the clean gas inlet 4 and the discharge channel 40 for feeding clean gas into the ionization chamber 6. In an alternative embodiment the clean gas channel 32 may be connected to another clean gas source.

The sample supply connection 50 is arranged to supply the sample aerosol from the sample supply channel 52 to the sample channel 34 as a swirling sample aerosol flow. The supply connection 50 is arranged to supply the sample aerosol from the sample supply channel 52 to the sample supply connection 50 tangentially in relation to the first supply direction for proving the swirling sample aerosol flow. As shown in FIG. 1 the sample supply channel 52 is connected to the sample channel 34 via the sample supply connection 50 and the sample supply connection is arranged between the sample supply channel 52 and the sample channel 34.

FIG. 2 shows the sample supply connection 50 in more detail.

The sample channel 34 has a first central axis extending in the first supply direction and is connected to the sample supply connection 50 in the first supply direction. The sample supply channel 52 is connected to the sample supply connection in a second supply direction transverse to the first supply direction. As shown in FIG. 1, the first supply direction is the main flow direction through the apparatus 1. The apparatus 1 has a stacked structure in which the components of the apparatus are successively or superposed and the sample aerosol flows in the first supply direction though the apparatus from the sample channel 34 to the discharge channel 40.

As shown in FIG. 2, the sample supply connection 50 is a tangential connection of the sample supply channel 52 to the sample channel 34 in relation to the first supply direction for providing the swirling aerosol flow around the first central axis along the sample channel 34. Accordingly, the sample channel 34 may have a first central axis extending in the first supply direction and circular or elliptical cross-section provided by sample channel side wall, and the sample supply connection 50 is a tangential connection of the sample supply channel 52 to the sample channel side wall in relation to the first central axis for providing the swirling aerosol flow around the first central axis along the sample channel 34.

Accordingly the sample supply channel connects tangentially to the sample channel for providing the sample supply connection 50.

In FIG. 2, the second supply direction is perpendicular to the first supply direction, but may also be inclined or transverse in an angle to the first supply direction.

In an alternative embodiment the sample supply connection 50 may comprise a sample supply chamber arranged between the sample supply channel 52 and the sample channel 34 and may be arranged to receive the sample aerosol in the second supply direction from the sample supply channel 52 and to supply the sample aerosol to the sample channel 34 extending in the first supply direction as a swirling or rotating sample aerosol flow. Accordingly, in this embodiment the sample supply channel 53 is connected tangentially to the sample supply chamber.

The sample supply chamber may a second central axis extending in the first supply direction. The second central axis may coincide with the first central axis of the sample channel 34. Thus the sample supply chamber may be arranged to provide the swirling sample aerosol flow around the second central axis and to supply the sample aerosol to the sample channel 34 as the swirling or rotating sample aerosol flow.

The sample supply chamber may be a tubular or cylindrical sample supply chamber having the second central axis extending in the first supply direction and a circular or elliptical cross-section, or circular or elliptical sample supply chamber side wall, the swirling aerosol flow being arranged to flow around the second central axis. Therefore, the sample supply channel 52 may be connected tangentially to the sample supply chamber or tangentially to the circular or elliptical sample supply chamber side wall of the sample supply chamber.

The sample supply channel 52 may be connected to the sample supply chamber in the second supply direction which is transverse, perpendicular or transverse to the first supply direction.

The sample supply chamber may be a separate chamber provided between the sample supply channel 52 and the sample channel 34, or that the upper end of the sample channel 34 forms the sample supply chamber.

In a preferred embodiment the first supply direction is vertical direction and the second supply direction is horizontal direction. In an alternative embodiment the first supply direction is horizontal direction and the second supply direction is vertical direction.

The sample supply connection 50 or the sample supply chamber may further comprises one or more guide vanes provided inside or to inner walls of the sample supply connection 50 or sample supply chamber for providing the swirling sample aerosol flow to the sample channel 34. The guide vans may be arranged to turn the sample aerosol flow inside the sample supply connection to tangential direction for proving the swirling sample aerosol flow.

The present invention further provides a method for particle measurement with an apparatus for particles measurement. The method comprises feeding sample aerosol containing particles into the mixing chamber 16 along sample channel 34 and via a sample inlet 14 provided to a mixing chamber 16, the sample channel extending in a first supply direction, feeding ionized clean gas into the mixing chamber 16 via ionized gas outlet 12 and mixing ionized clean gas and sample aerosol in the mixing chamber 16 for electrically charging particles of the sample aerosol and providing mixed sample aerosol comprising electrically charged particles generated by the ionized clean gas. The method further comprise removing free ions not attached to particles from the mixed sample aerosol and measuring electric current carried by the electrically charged particles. In one embodiment the electrically particles are filtered from the mixed sample aerosol and the electric current carried by the electrically charged particles is measured by measuring the current deposited to the filter with the electrically charged particles.

The method further comprises supplying sample aerosol to the sample channel 34 via the sample supply connection 50 from the second supply direction transverse to the first supply direction such that a swirling sample aerosol flow is generated to the sample channel 34 in relation to the first supply direction. Thus the sample aerosol is supplied tangentially to the sample supply connection 50 from the second supply direction transverse to the first supply direction for providing the swirling sample aerosol flow to the sample channel 34 in relation to the first supply direction.

Figure 3:
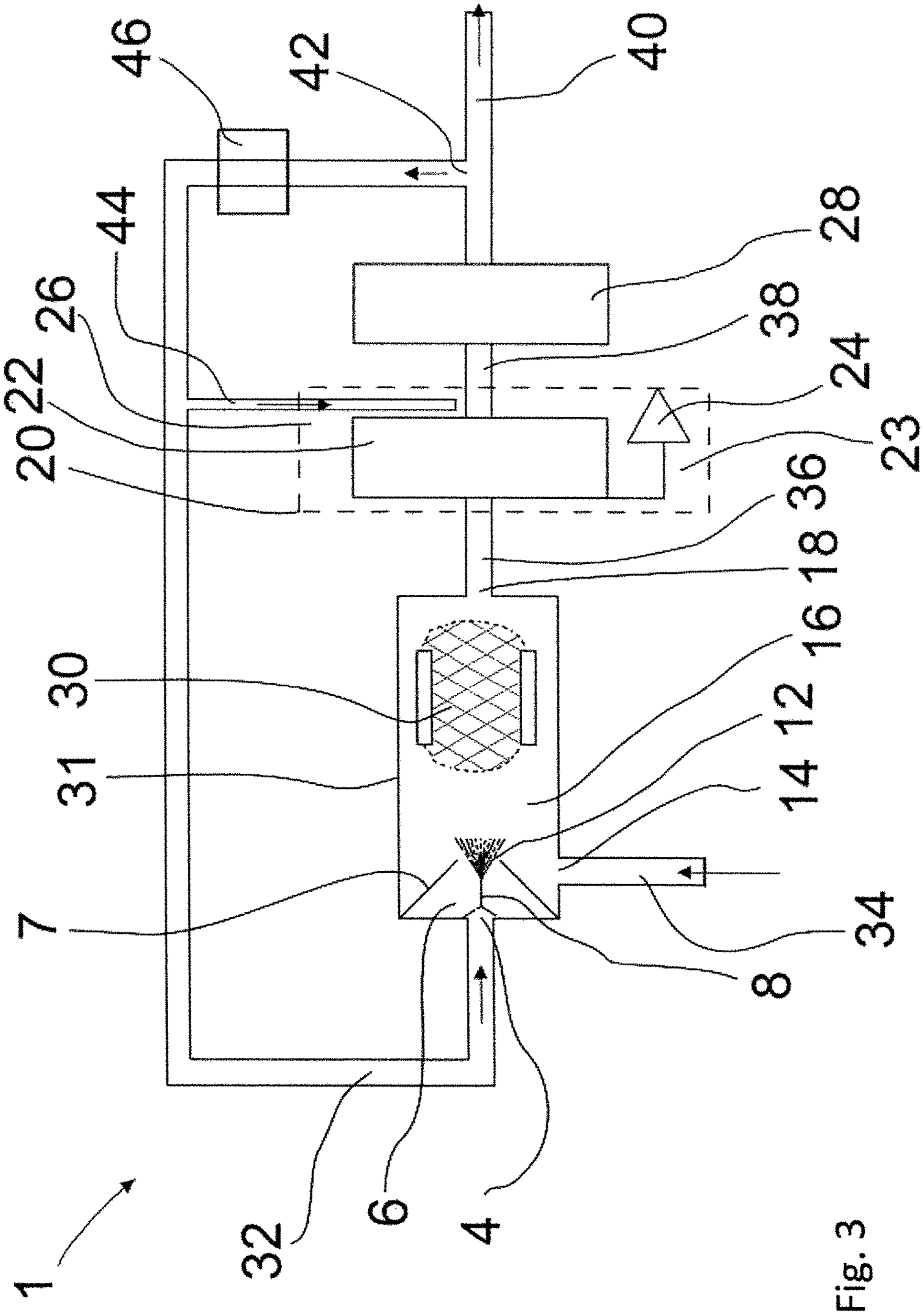
FIG. 3 shows one embodiment of an apparatus for particle measurement according to the present invention.
Figure 4:
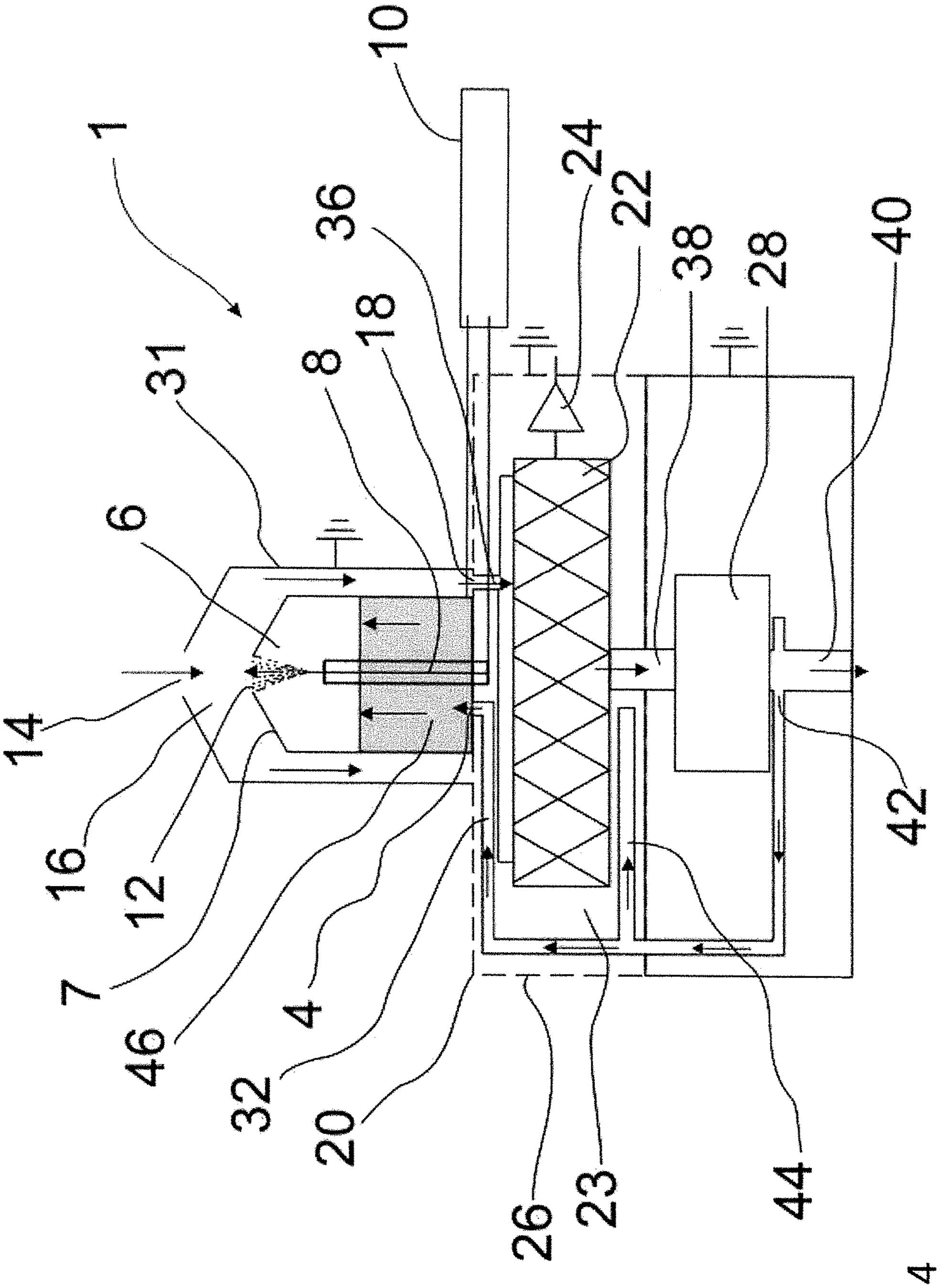
FIG. 4 shows another embodiment of an apparatus for particle measurement according to the present invention.

The following paragraphs relate to FIGS. 3 and 4.

FIGS. 3 and 4 show an apparatus comprising an ionization chamber having a clean gas inlet for feeding clean gas into the ionization chamber, a charging element arranged in the ionization chamber for charging the clean gas into ionized clean gas, and an ionized gas outlet for discharging the ionized clean gas from the ionization chamber, and a mixing chamber comprising a sample inlet for feeding sample aerosol into the mixing chamber, said mixing chamber is in a fluid communication with the ionization chamber for feeding ionized clean gas from the ionization chamber into the mixing chamber, and a mixing chamber outlet for discharging mixed sample aerosol formed in the mixing chamber by mixing ionized clean gas and sample aerosol, said mixed sample aerosol comprising electrically charged particles. The apparatus further comprises an ion trap for removing free ions not attached to particles from the mixed sample aerosol, a filter unit arranged to filter electrically charged particles from the mixed sample aerosol for forming filtered mixed sample aerosol, said filter unit comprising a filter and a housing, said filter unit is in fluid communication with the mixing chamber and arranged downstream of the mixing chamber, a pump for generating flow of clean gas, ionized clean gas, sample aerosol, mixed sample aerosol and filtered mixed sample aerosol, said pump is in fluid communication with the filter unit and arranged down-stream of the filter unit, a discharge channel connected to the pump for discharging filtered mixed sample aerosol from the apparatus. Accordingly the apparatus further comprises a sheath gas channel arranged in connection with filter unit, the sheath gas channel arranged to supply sheath gas inside the filter unit and downstream of the filter.

In one embodiment the sheath gas channel is arranged to supply sheath gas inside the filter unit downstream of the filter and between the filter and the housing. Thus the sheath gas channel may be arranged to extend from outside of the housing into the filter unit downstream of the filter or from outside of the housing into the filter unit downstream of the filter and between the filter and the housing.

In another embodiment the filter unit comprises an electrical insulator provided between the housing and the filter, and that the sheath gas channel is arranged to supply sheath gas inside the filter unit downstream of the filter and inside the electrical insulator, or inside the filter unit downstream of the filter and between the filter and electrical insulator, or inside the filter unit downstream of the filter and between the electrical insulator and the housing. Therefore the sheath gas channel may be arranged to extend from outside of the housing into the filter unit downstream of the filter and inside the electrical insulator, or downstream of the filter and between the filter and electrical insulator, or downstream of the filter and between the electrical insulator and the housing.

In one embodiment the apparatus further may comprise a filter output channel for discharging the filtered mixed sample aerosol from the filter, or a filter output channel for discharging the filtered mixed sample aerosol from the filter, the filter output channel extending from the filter inside the housing to outside the housing, or a filter output channel for discharging the filtered mixed sample aerosol from the filter, the filter output channel extending from the filter inside the housing to out-side the housing, the filter output channel being made of insulating material. In this case the sheath gas channel may be arranged to supply sheath gas to the outer surface of the filter output channel, or the sheath gas channel is arranged to supply sheath gas to the outer surface of the filter output channel and around the outer surface of the filter output channel. Therefore, the sheath gas channel may be arranged to extend to the filter output channel for supplying sheath gas to the outer surface of the filter output channel, or the sheath gas channel may be arranged to extend to the filter output channel and around the filter output channel for supplying sheath gas to the outer surface of the filter output channel and around the outer surface of the filter output channel. The filter may be supported to the filter unit or the housing with the filter output channel.

In yet another embodiment the apparatus may further comprise a sheath gas source and the sheath gas channel may be connected to the sheath gas source for supplying sheath gas into the filter unit, or the apparatus may further comprise a clean gas source and the sheath gas channel may be connected to the clean gas source for supplying sheath gas into the filter unit, the clean gas forming the sheath gas, or the apparatus may comprises a clean gas channel and the sheath gas channel may be connected to the clean gas channel for supplying sheath gas into the filter unit, the clean gas forming the sheath gas. In this case the clean gas channel may be connected to the clean gas inlet for feeding clean gas into the ionization chamber, and the sheath gas channel may be a branch channel of the clean gas channel. Furthermore, the clean gas channel may extend between the clean gas inlet and the discharge channel for feeding clean gas into the ionization chamber, or between the clean gas inlet and the pump for feeding clean gas into the ionization chamber.

The clean gas channel may comprise an additional clean gas filter. The additional clean gas filter may be arranged in connection with the clean gas channel between the discharge channel and the clean gas inlet. In an alternative embodiment the clean gas channel may comprise an additional clean gas filter and the additional clean gas filter may be arranged in connection with the clean gas channel between the discharge channel and the sheath gas channel.

The sheath gas channel may be arranged to supply the sheath gas from downstream of the filter to upstream of the filter for filtering the sheath gas. Thus the sheath gas channel extends from the downstream of the filter to upstream of the filter for filtering the sheath gas.

The sheath gas channel arranged in connection with the filter unit and downstream of the filter effectively prevents contamination from the clean side of the filter unit and the apparatus. The sheath gas can prevent contaminants and particles from passing further in the apparatus and further the sheath gas may keep the filter unit, electrical insulators and filter output channel clean by supplying clean gas. Thus the sheath gas further enables prevention of contamination also inside the filter unit and inside the housing the filter unit which cannot be achieved with prior art apparatuses.

FIG. 3 shows one embodiment of an apparatus 1 for particle measurement according to the present invention. The apparatus 1 comprises an ionization chamber 6 having a clean gas inlet 4 via which clean gas is supplied into the ionization chamber 6. The clean gas in the context of this application means essentially particle free gas. The ionization chamber 6 is further provided with electrical charging element 8 which is arranged to electrically charge the clean gas during or after supplying the clean gas via the clean gas inlet 4 into the ionization chamber 6. The electrical charging element 8 is connected to charging voltage source (not shown) for providing charging voltage to the electrical charging element 8. The electrical charging element electrically charges the clean gas as it passes the electrical charging element 8. Thus the ionization chamber 6 provides an ionized clean gas flow into the apparatus.

In one embodiment of the apparatus 1 the electrical charging element 8 is a corona electrode and the charging voltage source is a corona voltage source.

The clean gas is supplied to the ionization chamber 6 via clean gas channel 32 and the clean gas enters the ionization chamber 6 from the clean gas inlet 4 provided to the ionization chamber 6. The electrical charging element 8 is provided into the ionization chamber 6 such that the clean gas flow passes the electrical charging element 8 as it flows through the ionization chamber 6. The electrical charging element 8, or corona electrode, may be arranged for example to extend inside the charging chamber 6, as shown in FIG. 3. In one embodiment the electrical charging element 8 may be arranged to extend in the centre of the ionization chamber 6. The electrical charging element 8 may be a rod or wire which is electrically connected to the charging voltage source. Accordingly, the ionization of the clean gas is carried out in the ionization chamber 6. The ionization chamber 6 further comprises an ionized gas outlet 12 via which the ionized clean gas is discharged from the ionization chamber 6.

The ionization chamber 6 comprises chamber walls 7 defining the ionization chamber 6. The clean gas inlet 4 and the ionized gas outlet 12 may be arranged such that the clean gas flow flows through the ionization chamber 6 passing the electrical charging element 8 between the clean gas inlet 4 and the ionized gas outlet 12. In one embodiment the clean gas inlet 4 and the ionized gas outlet 12 are arranged opposite each other in the ionization chamber 6 and the electrical charging element 8 is arranged between the clean gas inlet 4 and the ionized gas outlet 12, as shown in FIG. 3. Thus the ionization chamber is provided as flow-through chamber in which the clean gas flows through the ionization chamber 6 from the clean gas inlet 4 directly to the ionized gas outlet 12. In the embodiment of FIG. 3 the ionization chamber walls 7 are arranged to converge towards the ionized gas outlet 12. Thus the ionization chamber 6 tapers towards the ionized gas outlet 12. The ionization chamber 6 may be therefore arranged to taper from the clean gas outlet 4 towards the ionized gas outlet 12 for providing ionized clean gas flow from the ionization chamber 6.

In an alternative embodiment the clean gas inlet 4 and the ionized gas outlet 12 are arranged to the ionization chamber wall 7 transversely or perpendicularly in relation to each other.

In an alternative embodiment the ionization chamber 6 may be omitted and the ionization chamber 6 may be arranged or integrated to the clean gas channel 32. In this case the electrical charging element 8 may be provided to the clean gas channel 32 such that the clean gas is ionized inside the clean gas channel 32 or at the clean gas inlet 4. In this embodiment ionized clean gas in supplied via the clean gas inlet 4.

The apparatus 1 of FIG. 3 further comprises a sample inlet 14 via which sample aerosol flow is supplied into the apparatus 1. The sample aerosol flow is supplied in to the apparatus 1 via sample channel 34 from a space comprising aerosol to be measured with the particle measurement apparatus 1. The space may be a habitable space, industrial space, process chamber, ventilation system, combustion system, exhaust conduit or any other space comprising particle containing aerosol.

The apparatus 1 comprises a mixing chamber 16 in which the ionized clean gas flow and the particle containing sample aerosol flow meet each other and are mixed with each other for providing a mixed sample aerosol. The mixing chamber 16 is defined by mixing chamber walls 31. The ionized clean gas enters the mixing chamber 16 from the ionized gas outlet 12 and the sample aerosol flow enters the mixing chamber from the sample inlet 14. In the mixing chamber 16 the ionized clean gas flow and the sample aerosol flow collide or mix with each other such that the ionized clean gas electrically charges the particles of the sample aerosol providing mixed sample aerosol comprising electrically charged particles. The charging of the particles occurs mainly by diffusion charging such that ions in the ionized clean gas are attached to the particles and the particles become electrically charged.

In the embodiment of FIG. 3 the ionized clean gas enters the mixing chamber 16 from the ionized gas outlet 12 and the sample aerosol flow enters the mixing chamber from the sample inlet 14 transversely to ionized gas outlet 12 and the ionized clean gas flow such that the ionized clean gas and the sample aerosol collide to each other and become mixed. In the embodiment of FIG. 3 the ionized gas outlet 12 is arranged to a first end wall of the mixing chamber 16 and the ionized clean gas enters the mixing chamber 16 in a first flow direction. The sample inlet 14 is arranged to a side wall of the mixing chamber 16 and the sample aerosol enters the mixing chamber 16 in a second flow direction transversely or perpendicularly to the first flow direction of the ionized clean gas such that the ionized clean gas and the sample aerosol collide and are mixed inside the mixing chamber 16 for electrically charging the particles of the sample aerosol.

In an alternative embodiment the sample inlet 14 may be arranged to the first end wall of the mixing chamber 16 and the ionized gas outlet 12 to the side wall of the mixing chamber 16.

As shown in FIG. 3, the ionization chamber 6 is defined with the ionization chamber walls 7 and provided inside the mixing chamber 16. Thus the ionization chamber 6 is within the mixing chamber 16 and separated with the ionization chamber walls 7. In an alternative embodiment the ionization chamber may be provided upstream and separate of the mixing chamber 16 and the ionized clean gas is transported into the mixing chamber 16 from outside of the mixing chamber 16. In a yet alternative embodiment the ionization chamber 6 is provided to or formed by the clean gas channel 32.

According to the above mentioned the ionization chamber 6 is provided in fluid communication with mixing chamber 16 in all embodiments.

The mixing chamber 16 further comprises mixing chamber outlet 18 via which the mixed sample flow comprising electrically charged particles is discharged from the mixing chamber 16.

In FIG. 3, the mixing chamber outlet 18 is provided to the second end wall of the mixing chamber 16 opposite the ionized clean gas outlet 12. Therefore, the mixing chamber 16 is provided as flow-through chamber such that the ionized clean gas flow is directed in the first flow direction towards the mixing chamber outlet 18.

In an alternative embodiment the mixing chamber outlet 18 may be provided to a side wall of the mixing chamber 16. Thus the mixing chamber outlet 18 may be arranged opposite the sample inlet 14 or adjacent the sample inlet 14 or displaced relative to the sample inlet 14. Furthermore, also the sample inlet 14 may be provide to the first end wall of the mixing chamber 16, thus opposite the mixing chamber outlet 18 of FIG. 3.

The mixing chamber 16 is further provided with ion trap 30 for removing free ions not attached to the particles of the mixed sample aerosol. The ion trap 30 is provided as an ion trap electrode or electrodes having opposite polarity than the free ions. The ion trap electrode may be any kind of electrode, for example such as plate-like electrode or net-like electrode. The ion trap electrode may be connected to an ion trap voltage source or it may be grounded such that electric field is provided between the electrical charging element 8 and the ion trap electrode for collecting the free ions not attached to the particles. The ion trap voltage is high enough to deposit the free ions, but due to the lower mobility the electrically charged particles are not deposited to the ion trap electrode.

The ion trap 30 is provided downstream of the ionized gas outlet 12 and the sample inlet 14 such that the ionized clean gas and the sample aerosol are mixed and the particles electrically charged before the mixed sample aerosol meets the ion trap 30 and is subjected to the ion trap voltage. As shown in FIG. 3, the ion trap is provided inside mixing chamber 16 upstream of the mixing chamber outlet 18, or between the ionized gas outlet 12 and the sample inlet 14, and the mixing chamber outlet 18.

In an alternative embodiment the ion trap 30 may be arranged downstream of the mixing chamber 16 and downstream of the mixing chamber outlet 18. Thus in this embodiment the ion trap 30 is separate from the mixing chamber 16.

The apparatus 1 further comprises a filter unit 20 arranged downstream of the mixing chamber 16, as shown in FIG. 3. The filter unit 20 is arranged in fluid communication with the mixing chamber 16 and downstream of the mixing chamber 16. In the embodiment of FIG. 3, the filter unit 20 is connected to the mixing chamber 16 with filter inlet channel 36 for passing the mixed sample aerosol flow from the mixing chamber 16 to the filter unit 20. Therefore, the mixed sample aerosol flow is passed from the mixing chamber 16 via the mixing chamber outlet 18 and the filter inlet channel to the filter unit 20.

It should be noted that the ion trap 30 is provided upstream or before of the filter unit 20. In FIG. 3, the ion trap 30 is provided inside the mixing chamber 16. In an alternative embodiment the ion trap 30 may also be provided to the filter inlet channel 36 between the mixing chamber 16 and the filter unit 20.

The filter unit 20 comprises a housing 26 inside which a filter 22 is arranged. The housing 20 comprises or is formed as a faraday cage for electrically separating the filter unit 20 from the other parts of the apparatus 1, and especially from the ionization chamber 6, electrical charging element 8, ion trap 30 and the mixing chamber 16. The filter unit 20 further comprises an electrical insulator 23 inside the housing 20. The filter 22 may embedded inside the insulator 23 for further electrically insulating the filter 22 from the other parts of the apparatus. Thus the insulator 23 may surround the filter. In an alternative embodiment the insulator 23 may be provided inside the housing 26 upstream of the filter 22 or downstream of the filter 22, or upstream and downstream of the filter 22. Furthermore, the insulator 23 may also be provided on the lateral sides of the filter 22. The filter 22 may be any kind of conventional filter, such as a membrane filter or some other kind of filter. The structure of the filter unit is arranged such that the filter 22 may be removed from the filter unit 20 and replaced or changed to a new filter 22. Thus the housing 26 is arranged to be opened and closed.

The electrically charged particles of the mixed sample aerosol are filtered and removed from the mixed sample aerosol flow in the filter 22. During the filtration with the filter 22 the electrically charged particles are deposited to the filter 22 and accumulate to the filter 22.

As the electrically charged particles are deposited to the filter 22 they generate electrical current to the filter 22. The filter unit 20 therefore further comprises electrical measurement element 24 connected to the filter 22. The electrical measurement element 24 is arranged to measure the electrical current produced by the electrically charged particles in the filter 22 as they are deposited to the filter 22. The electrical measurement element 24 provides an output signal based on the measurement results of the electrical current measurements from the filter 22. The output signal may be transmitted to a processing unit (not shown) for further analysis. The electrical measurement element 24 may comprise an electrometer or the like measuring device.

The ion trap 30 has to be arranged upstream of or before the filter unit 20 such that the free ions present invention mixed sample aerosol do not affect the particle measurement based on the measuring the electrical current carried by the electrically charged particles.

In the filter unit 20 the electrically charged particles are filtered from the mixed sample aerosol and a filtered mixed sample aerosol flow is discharged from the filter unit 20.

Downstream of the filter unit 20 is provided a pump 28 or other kind of suction device. The pump 28 is arranged in fluid communication with the filter unit 20 and arranged downstream of the filter unit 20. The pump 28 is arranged to generate flow of at least sample aerosol, mixed sample aerosol and filtered mixed sample aerosol through the apparatus 1. The pump 28 may also be arranged to generate flow of the clean gas and ionized clean gas into or in the apparatus 1.

The pump 28 is connected to the filter unit 20 with a filter output channel 38 extending between the filter unit 20 and the pump 28 for passing the filtered mixed sample aerosol from the filter unit 20 to the pump 28. The filtered mixed sample aerosol is discharged from the pump 28 and from the apparatus 1 via discharge channel 40. The filtered mixed sample aerosol may be discharged via the discharge channel 40 out of the apparatus 1 to environment or back to the space from where it was taken.

The apparatus further comprises a sheath gas channel 44 arranged in connection with filter unit 20. The sheath gas channel 44 is arranged to supply sheath gas inside the filter unit 20 and downstream of the filter 22. The sheath gas prevents contamination from passing further in the apparatus and also keeps the downstream side of filter free of contamination and particles.

As shown in FIG. 3, the sheath gas channel 44 is arranged to supply sheath gas inside the filter unit 20 downstream of the filter 22 and between the filter 22 and the housing 26. The sheath gas channel is therefore arranged to extend from outside of the housing 26 into the filter unit 20 downstream of the filter 22, and further between the filter 22 and the housing 26. This enables the downstream side of the filter to be protected against contamination.

The filter unit 20 may also in some embodiments comprise an electrical insulator 23 provided between the housing 26 and the filter 22 for electrically insulating the filter from the housing 26. The electrical insulation is important as the particle measurement is carried out by measuring the electric current carried by the electrically charged particles to the filter 22. In this case the sheath gas channel 44 may be arranged to supply sheath gas inside the filter unit 20 downstream of the filter 22 and inside the electrical insulator 23 such that the sheath gas channel 44 extends from outside of the housing 26 into the filter unit 20 downstream of the filter 22 and inside the electrical insulator 23. Thus the contamination may be prevented from passing between the electrical insulator 23 and the housing 26.

In an alternative embodiment the sheath gas channel 44 may be arranged to supply sheath gas inside the filter unit 20 downstream of the filter 22 and between the filter 22 and electrical insulator 23 such that the sheath gas channel 44 extends from outside of the housing 26 into the filter unit 20 downstream of the filter 22 and between the filter 22 and electrical insulator 23. Therefore the sheath gas prevents the electrical insulator 23 from being subjected to contamination and particles.

In yet alternative embodiment the sheath gas channel 44 may be arranged to supply sheath gas inside the filter unit 20 downstream of the filter 22 and between the electrical insulator 23 and the housing 26 such that sheath gas channel 44 extends from outside of the housing 26 into the filter unit 20 downstream of the filter 22 and between the electrical insulator 23 and the housing 26. Thus the sheath gas prevents the contamination from passing to the housing 26 downstream of the filter 22 and also escaping from the housing 26 downstream of the filter 22.

The sheath gas channel 44 may be arranged to supply the sheath gas from downstream of the filter 22 to upstream of the filter 22 for filtering the sheath gas. Thus the sheath gas channel 44 extends from the downstream of the filter 22 to upstream of the filter 22 for filtering the sheath gas.

The sheath gas channel 44 may be pipe or the like or alternative it may be provided by machining the filter unit 22 for providing bores or the like. The sheath gas channel 44 may thus be integral feature of the filter unit 20, and provided for example to the electrical insulator 23 or by forming the electrical insulator 23.

The filtered mixed sample aerosol is discharged from the filter unit 20 and the filter 22 via the filter output channel 38. As shown in FIG. 3, the filter output channel 38 extends from the filter 22 inside the housing 26 to outside the housing 26. In some embodiments the filter output channel 38 may be made of electrically insulating material such that filter 22 and the filter unit 20 may be electrically insulated from the other parts of the apparatus effectively. In some embodiments the filter output channel 38 may be made of insulator sleeve. The filter output channel 44 may therefore be also used for supporting the filter 22 to the filter unit 20 or to the housing 26.

In this embodiment the sheath gas channel 44 may be arranged to supply sheath gas to the outer surface of the filter output channel 38 such that the sheath gas channel 44 is arranged to extend to the filter output channel 38 for supplying sheath gas to the outer surface of the filter output channel 38. This may also be achieved such the sheath gas channel 44 is arranged to supply sheath gas to the outer surface of the filter output channel 38 and around the outer surface of the filter output channel 38. Therefore the sheath gas channel 44 is arranged to extend to the filter output channel 38 and around the filter output channel 38 for supplying sheath gas to the outer surface of the filter output channel 38 and around the outer surface of the filter output channel 38. This enables the filter output channel 38 free on contamination and thus prevents the sensitive insulator material of the filter output channel from deteriorating. Then there is clean gas on both sides, on the inner surface and outer surface, of the filter output channel 38.

The apparatus may comprise a separate sheath gas source and the sheath gas channel 44 may be connected to the sheath gas source for supplying sheath gas into the filter unit 20. Alternatively, if the apparatus comprises a clean gas source, the sheath gas channel 44 may be connected to the clean gas source for supplying sheath gas into the filter unit 20. The clean gas forms the sheath gas.

As shown in FIG. 3, the apparatus 1 comprises a clean gas channel 32 and the sheath gas channel 44 is connected to the clean gas channel 32 for supplying sheath gas into the filter unit 20.

In the embodiment of FIG. 3 the clean gas channel 32 is connected to the clean gas inlet 4 for feeding clean gas into the ionization chamber 6 and the sheath gas channel 44 is a branch channel of the clean gas channel 32.

In the apparatus of FIG. 3, the clean gas channel 32 extends between the clean gas inlet 4 and the discharge channel 40 for feeding clean gas into the ionization chamber 6. Alternatively the clean gas channel 32 may extend between the clean gas inlet 4 and the pump 28 for feeding clean gas into the ionization chamber 6. Thus the filtered mixed aerosol is used as clean for the ionization chamber 6 and no separate clean gas source is needed or separate filter for producing clean gas is not needed. However, the clean gas channel 32 may also comprise an additional clean gas filter 46. The additional clean gas filter 46 may be arranged in connection with the clean gas channel 32 between the discharge channel 40 and the clean gas inlet. The additional clean gas filter 46 may be arranged between the discharge channel 40 and the sheath gas channel 44.

FIG. 4 shows another embodiment of an apparatus 1 for particle measurement according to the present invention. It should be noted that construction of the apparatus of FIG. 4 is different from the construction of apparatus of FIG. 3, but similar parts are denoted with same reference numerals. Furthermore, the same principles of operation and purpose of different parts apply to both embodiment of the apparatus and also to other possible modifications of the apparatus according to the present invention.

The apparatus 1 of FIG. 4 comprises an ionization chamber 6 for supplying clean ionized gas into the apparatus 1. The clean gas in the context of this application means essentially particle free gas. The ionization chamber 6 comprises a clean gas inlet 4 via which the clean gas is supplied into the ionization chamber 6. The ionization chamber 6 is further provided with electrical charging element 8 which is arranged to electrically charge the clean gas during or after supplying the clean gas via the clean gas inlet 4 into the apparatus 1. The electrical charging element 8 is connected to charging voltage source 10 for providing charging voltage to the electrical charging element 8. The charging voltage source 10 may be any kind voltage source, such as high voltage source. The electrical charging element 8 electrically charges the clean gas as it passes the electrical charging element 8. Thus the blow charger provides an ionized clean gas flow into the apparatus 1.

In one embodiment of the apparatus 1 of FIG. 4 the electrical charging element 8 is a corona electrode and the charging voltage source 10 is a corona voltage source.

The clean gas is supplied to the ionization chamber 6 via clean gas channel 32 and the clean gas enters the ionization chamber 6 from the clean gas inlet 4 provided to the ionization chamber 6. The electrical charging element 8 is provided into the ionization chamber 6 such that the clean gas flow passes the electrical charging element 8 as it flows through the ionization chamber 6. The electrical charging element 8, or corona electrode, may be arranged for example to extend inside the charging chamber 6, as shown in FIG. 4. In one embodiment the electrical charging element 8 may be arranged to extend in the centre of the ionization chamber 6. The electrical charging element 8 may be a rod or wire which is electrically connected to the charging voltage source. Accordingly, the ionization of the clean gas is carried out in the ionization chamber 6. The ionization chamber 6 further comprises an ionized gas outlet 12 via which the ionized clean gas is discharged from the ionization chamber 6.

The ionization chamber 6 comprises chamber walls 7 defining the ionization chamber 6. The clean gas inlet 4 and the ionized gas outlet 12 may be arranged such that the clean gas flows through the ionization chamber 6 passing the electrical charging element 8 between the clean gas inlet 4 and the ionized gas outlet 12. In one embodiment the clean gas inlet 4 and the ionized gas outlet 12 are arranged opposite each other in the ionization chamber 6 and the electrical charging element 8 is arranged between the clean gas inlet 4 and the ionized gas outlet 12, as shown in FIG. 4. Thus the ionization chamber is provided as flow-through chamber in which the clean gas flows through the ionization chamber 6 from the clean gas inlet 4 directly to the ionized gas outlet 12. In the embodiment of the apparatus of FIG. 4 the ionization chamber walls 7 are arranged converge towards the ionized gas outlet 12. Thus the ionization chamber 6 tapers towards the ionized gas outlet 12. The ionization chamber 6 therefore may be arranged to taper from the clean gas outlet 4 towards the ionized gas outlet 12 for providing ionized clean gas flow from the ionization chamber 6.

In an alternative embodiment the clean gas inlet 4 and the ionized gas outlet 12 are arranged to the ionization chamber wall 7 transversely or perpendicularly in relation to each other.

In an alternative embodiment the separate ionization chamber 6 may be omit-ted and the ionization chamber 6 may be arranged or integrated to the clean gas channel 32. In this case the electrical charging element 8 may be provided to the clean gas channel 32 such that the clean gas is ionized inside the clean gas channel 32 or at the clean gas inlet 4. In this embodiment ionized clean gas in supplied via the clean gas inlet 4.

The apparatus 1 further comprises a sample inlet 14 via which sample aerosol flow is supplied into the apparatus. The sample aerosol flow is supplied into the apparatus from a space comprising aerosol to be measured with the particle measurement apparatus 1. The space may be a habitable space, industrial space, process chamber, ventilation system, combustion system, exhaust conduit or any other space comprising particle containing aerosol.

The apparatus 1 comprises a mixing chamber 16 in which the ionized clean gas and the particle containing sample aerosol meet each other and are mixed with each other for providing a mixed sample. The mixing chamber 16 is defined by mixing chamber walls 31. The ionized clean gas enters the mixing chamber 16 from the ionized gas outlet 12 and the sample aerosol enters the mixing chamber from the sample inlet 14. In the mixing chamber 16 the ionized clean gas and the sample aerosol collide and mix with each other such that the ionized clean gas electrically charges the particles of the sample aerosol providing a mixed sample aerosol comprising electrically charged particles. The charging of the particles occurs mainly by diffusion charging such that ions in the ionized clean gas are attached to the particles and the particles become electrically charged.

In the embodiment of FIG. 4 the ionized clean gas enters the mixing chamber 16 from the ionized gas outlet 12 and the sample aerosol enters the mixing chamber 16 from the sample inlet 14 opposite the ionized gas outlet 12 and ionized clean gas flows such that the ionized clean gas and the sample aerosol collide to each other and becomes mixed. In the embodiment of FIG. 4 the ionized gas outlet 12 is arranged towards and opposite the sample inlet 14 and the ionized clean gas enters the mixing chamber 16 in a first flow direction. The sample inlet 14 is arranged towards and opposite the ionized gas outlet 12 and the sample aerosol enters the mixing chamber 16 in a second flow direction opposite the first flow direction of the ionized clean gas such that the ionized clean gas and the sample aerosol collide directly against each other and are mixed inside the mixing chamber 16 for electrically charging the particles of the sample aerosol. In other words, arranging the ionized gas outlet 12 and the sample inlet 14 opposite each other provides countercurrent flow of the ionized clean gas and the sample aerosol inside the mixing chamber 16. Thus the ionized clean gas and the sample aerosol may collide directly against each other in a collision angle of substantially 180 degrees.

As shown in FIG. 4, the ionization chamber 6 is defined with the ionization chamber walls 7 and provided inside the mixing chamber 16. Thus the ionization chamber 6 is within the mixing chamber 16 and separated with the ionization chamber walls 7. The mixing chamber 16 and the mixing chamber walls 31 surround the ionization chamber 6. Therefore the ionization chamber 6 is nested inside the mixing chamber 16. There is gap between the ionization chamber walls 7 and the mixing chamber walls 31, as shown in FIG. 4, for providing a flow path for the mixed sample aerosol flow comprising electrically charged particles.

In an alternative embodiment the ionization chamber may be provided outside of the mixing chamber 16 and the ionized clean gas in transported into the mixing chamber from outside of the mixing chamber 16. In a yet alternative embodiment the ionization chamber 6 is provided to or formed by the clean gas channel 32.

According to the above mentioned the ionization chamber 6 is provided in fluid communication with mixing chamber 16 in all embodiments of the apparatus according to the FIG. 4.

The mixing chamber 16 further comprises mixing chamber outlet 18 via which the mixed sample aerosol comprising electrically charged particles is discharged from the mixing chamber 16. The mixed sample aerosol flows from the flow path between the ionization chamber walls 7 and the mixing chamber walls 31 to mixing chamber outlet 18 and discharges from the mixing chamber 16.

In FIG. 4, the sample inlet 14 is provided to a first end or first end wall of the mixing chamber 16 and the mixing chamber outlet 18 is provided to a second end or second end wall of the mixing chamber 16 opposite the sample inlet 14. Therefore, the mixing chamber 16 is provided as flow-through chamber such that the sample aerosol flows through the mixing chamber 16 and directed in the second flow direction towards the mixing chamber outlet 18.

In an alternative embodiment the mixing chamber outlet 18 may be provided to a side wall of the mixing chamber 16 transversely or perpendicularly to the sample inlet 14.

The mixing chamber 16 is further provided with ion trap 30 for removing free ions not attached to the particles of the mixed sample aerosol. In the embodiment of FIG. 4 the ion trap is provided by the mixing chamber walls 31. Thus the mixing chamber walls 31 forms the ion trap or an ion trap electrode. As shown in FIG. 4, the charging voltage source 10 is electrically connected to the electrical charging element 8 and to the ionization chamber walls 7. Thus the electrical charging element 8 and the ionization chamber walls 7 are at same electrical potential. The mixing chamber walls 31 are grounded such that the mixing chamber walls 31 form the ion trap electrode for collecting and removing free ions from the mixed sample aerosol as the mixed sample aerosol passes the mixing chamber walls 31 between the ionization chamber 6 and the mixing chamber 16. Therefore, an electric field is provided between the ionization chamber walls 7 and the mixing chamber walls 31.

The ion trap, or the mixing chamber walls 31, is thus provided as an ion trap electrode or electrodes having opposite polarity than the free ions. Alternative the mixing chamber 16 may be provided with separate electrode or electrodes formed as ion trap electrodes. The separate ion trap electrode may be any kind of electrode, for example such as plate-like electrode or net-like electrode. The ion trap electrode may also be connected to an ion trap voltage source or it may be grounded such that electric field is provided between the electrical charging element 8 and the ionization chamber wall 7, and the ion trap electrode for collecting the free ions not attached to the particles. The ion trap voltage is high enough to deposit the free ions, but due to the lower mobility the electrically charged particles are not deposited to the ion trap electrode.

The ion trap is provided such that the ionized clean gas and the sample aerosol are mixed and the particles electrically charged before the mixed sample aerosol meets the ion trap and is subjected to the ion trap voltage.

In an alternative embodiment the ion trap may be arranged downstream of the mixing chamber 16 and downstream of the mixing chamber outlet 18. Thus in this embodiment the ion trap is separate from the mixing chamber 16.

The apparatus 1 further comprises a filter unit 20 arranged downstream of the mixing chamber 16, as shown in FIG. 4. The filter unit 20 is arranged in fluid communication with the mixing chamber 16 and downstream of the mixing chamber 16. In the embodiment of FIG. 4, the filter unit 20 is connected to the mixing chamber 16 with filter inlet channel 36 for passing the mixed sample aerosol flow from the mixing chamber 16 to the filter unit 20. Therefore, the mixed sample aerosol flow is passed from the mixing chamber 16 via the mixing chamber outlet 18 and the filter inlet channel 36 to the filter unit 20.

It should be noted that the ion trap 30 is provided upstream or before of the filter unit 20. In FIG. 3, the ion trap 30 is provided inside the mixing chamber 16. In an alternative embodiment the ion trap 30 may also be provided to the filter inlet channel 36 between the mixing chamber 16 and the filter unit 20.

The filter unit 20 comprises a housing 26 inside which a filter 22 is arranged. The housing 20 comprises or is formed as a faraday cage for electrically separating the filter unit 20 from the other parts of the apparatus 1, and especially from the ionization chamber 6, electrical charging element 8, the ion trap and the mixing chamber 16. The filter unit 20 further comprises an electrical insulator 23 inside the housing 20. The filter 22 is embedded inside the insulator 23 for further electrically insulating the filter 22 from the other parts of the apparatus 1. The filter 22 may be any kind of conventional filter, such as membrane filter or some other kind of filter. The structure of the filter unit 20 is arranged such that the filter 22 may be removed from the filter unit 20 and replaced or changed to a new filter 22. Thus the filter unit 20 may be opened and closed.

The electrically charged particles of the mixed sample aerosol are filtered and removed from the mixed sample aerosol in the filter 22. During the filtration with the filter 22 the electrically charged particles are deposited to the filter 22 and accumulate to the filter 22.

As the electrically charged particles are deposited to the filter 22 they generate electrical current to the filter 22. The filter unit 20 therefore further comprises electrical measurement element 24 connected to the filter 22. The electrical measurement element 24 is arranged to measure the electrical current produced by the electrically charged particles in the filter 22 as they are deposited to the filter 22. The electrical measurement element 24 provides an output signal based on the measurement results of the electrical current measurements from the filter 22. The output signal may be transmitted to a process unit (not shown) for further analysis. The electrical measurement element 24 may comprise an electrometer or the like measuring device.

The ion trap has to be arranged upstream of or before the filter unit 20 such that the free ions present invention mixed sample aerosol do not affect the particle measurement based on the measuring the electrical current carried by the electrically charged particles.

In the filter unit 20 the electrically charged particles are filtered from the mixed sample aerosol and a filtered mixed sample aerosol flow is discharged from the filter unit 20.

Downstream of the filter unit 20 is provided a pump 28 or other kind of suction device. The pump 28 is arranged in fluid communication with the filter unit 20 and arranged downstream of the filter unit 20. The pump 28 is arranged to generate flow of at least sample aerosol, mixed sample aerosol and filtered mixed sample aerosol through the apparatus 1. The pump 28 may also be arranged to generate flow of the clean gas and ionized clean gas into or in the apparatus 1.

The pump 28 is connected to the filter unit 20 with a filter output channel 38 extending between the filter unit 20 and the pump 28 for passing the filtered mixed sample aerosol from the filter unit 20 to the pump 28. The filtered mixed sample aerosol is discharged from the pump 28 and from the apparatus 1 via discharge channel 40. The filtered mixed sample aerosol may be discharged via the discharge channel 40 out of the apparatus 1 to environment or back to the space from where it was taken.

As shown in FIG. 4, the apparatus comprises a flow through structure such that the sample aerosol flows in the second flow direction through the apparatus 1. This enables effective constructions and operation of the apparatus such that the size or height of the apparatus 1 may be minimized. This means the sample inlet 14, filter unit 20 and the pump 28 are arranged in line with each other. In one embodiment the sample inlet 14, mixing chamber 16, filter unit 20 and the pump 28 are all arranged in line with each other. In a yet alternative embodiment the sample inlet 14, mixing chamber 16, ionization chamber 6, filter unit 20, the pump 28 and the discharge channel 40 are all arranged in line with each other.

The apparatus 1 of FIG. 4 also comprises a sheath gas channel 44 arranged in connection with filter unit 20. The sheath gas channel 44 being arranged to supply sheath gas inside the filter unit 20 and downstream of the filter 22. The sheath gas channel 44 is arranged to extend from outside of the housing 26 into the filter unit 20 downstream of the filter 22 and between the filter 22 and the housing 26.

The filter unit 20 comprises an electrical insulator 23 provided between the housing 26 and the filter 22. The sheath gas channel 44 is arranged to supply sheath gas inside the filter unit 20 downstream of the filter 22 and to the electrical insulator 23 such that the sheath gas channel 44 is arranged to extend from outside of the housing 26 into the filter unit 20 downstream of the filter 22 and to the electrical insulator 23.

The filter output channel 38 extends from the filter 22 inside the housing 26 to outside the housing 26. The filter output channel 38 may be made of insulating material. The sheath gas channel 44 is arranged to supply sheath gas to the outer surface of the filter output channel 38 and around the outer surface of the filter output channel 38 such that the sheath gas channel 44 extends to the filter output channel 38 and around the filter output channel 38 for supplying sheath gas to the outer surface of the filter output channel 38 and around the outer surface of the filter output channel 38.

The filter 22 may be supported to the filter unit 20 or the housing 26 with the filter output channel 38. The sheath gas channel 44 may be further provided in fluid communication or connected to upstream of the filter 22 for filtering the sheath gas.

As shown in FIG. 4 the discharge channel 40 discharges the filtered mixed sample aerosol out from the apparatus 1. The discharge channel 40 comprises in this embodiment of the invention a clean gas intake 42 for feeding filtered mixed sample aerosol as a clean gas toward the ionization chamber 6. The clean gas intake 42 provides an opening for the clean gas channel 32. The embodiment of the invention shown in FIG. 4 does not have any additional clean gas filters in the clean gas channel 32 but instead the additional clean gas filter 46 is arranged in connection with the ionization chamber band the clean gas inlet 4 such that the clean gas supplied from the clean gas inlet 4 is fed through the additional clean gas filter 46 before being ionized in the ionization chamber 6. The additional clean gas filter 46 is arranged inside the ionization chamber 6. The clean gas channel 32 is connected to the clean gas inlet 4 for feeding clean gas into the ionization chamber 6, and that the sheath gas channel 44 is a branch channel of the clean gas channel 32. The clean gas channel 32 extends between the clean gas inlet 4 and the discharge channel 40 for feeding clean gas into the ionization chamber 6. The sheath gas channel 44 is connected to the clean gas channel 32 for supplying sheath gas into the filter unit 20. The clean gas forms the sheath gas. Thus the sheath gas source is provided by the apparatus 1, and no separate sheath gas source is needed.

According to the above mentioned and in relation to FIGS. 3 and 4, the apparatus 1 comprises; an ionization chamber 6 comprising a clean gas inlet 4 for feeding clean gas into the ionization chamber 6, a charging element 8 arranged in the ionization chamber 6 for charging the clean gas into ionized clean gas, and an ionized gas outlet 12 for discharging the ionized clean gas from the ionization chamber 6; a mixing chamber 16 comprising a sample inlet 14 for feeding sample aerosol into the mixing chamber 16, said mixing chamber 16 is in a fluid communication with the ionization chamber 6 for feeding ionized clean gas from the ionization chamber 6 into the mixing chamber 16, and a mixing chamber outlet 18 for discharging mixed sample aerosol formed in the mixing chamber 16 by mixing ionized clean gas and sample aerosol, said mixed sample aerosol comprising electrically charged particles; an ion trap 30 for removing free ions not attached to particles from the mixed sample aerosol; a filter unit 20 arranged to filter electrically charged particles from the mixed sample aerosol for forming filtered mixed sample aerosol, said filter unit 20 comprising a filter 22 and a housing 26, said filter unit 20 is in fluid communication with the mixing chamber 16 and arranged downstream of the mixing chamber 16; a pump 28 for generating flow of clean gas, ionized clean gas, sample aerosol, mixed sample aerosol and filtered mixed sample aerosol, said pump 28 is in fluid communication with the filter unit 20 and arranged downstream of the filter unit 20; a discharge channel 40 connected to the pump 28 for discharging filtered mixed sample aerosol from the apparatus 1; and a sheath gas channel 44 arranged in connection with filter unit 20, the sheath gas channel 44 being arranged to supply sheath gas inside the filter unit 20 and downstream of the filter 22.

The sheath gas channel 44 may be arranged to supply sheath gas inside the filter unit 20 downstream of the filter 22 and between the filter 22 and the housing 26. Furthermore, the sheath gas channel 44 may be arranged to extend from outside of the housing 26 into the filter unit 20 downstream of the filter 22 or to extend from outside of the housing 26 into the filter unit 20 downstream of the filter 22 and between the filter 22 and the housing 26.

The filter unit 20 may comprise an electrical insulator 23 provided between the housing 26 and the filter 22, and the sheath gas channel 44 may be arranged to: supply sheath gas inside the filter unit 20 downstream of the filter 22 and inside the electrical insulator 23; or supply sheath gas inside the filter unit 20 downstream of the filter 22 and between the filter 22 and electrical insulator 23; or supply sheath gas inside the filter unit 20 downstream of the filter 22 and between the electrical insulator 23 and the housing 26.

The sheath gas channel 44 may be arranged to: extend from outside of the housing 26 into the filter unit 20 downstream of the filter 22 and inside the electrical insulator 23; or extend from outside of the housing 26 into the filter unit 20 downstream of the filter 22 and between the filter 22 and electrical insulator 23; or extend from outside of the housing 26 into the filter unit 20 downstream of the filter 22 and between the electrical insulator 23 and the housing 26.

The apparatus 1 may further comprise: a filter output channel 38 for discharging the filtered mixed sample aerosol from the filter 22; or a filter output channel 38 for discharging the filtered mixed sample aerosol from the filter 22, the filter output channel 38 extending from the filter 22 inside the housing 26 to outside the housing 26; or a filter output channel 38 for discharging the filtered mixed sample aerosol from the filter 22, the filter output channel 38 extending from the filter 22 inside the housing 26 to outside the housing 26, the filter output channel 38 being made of insulating material.

The sheath gas channel 44 may be arranged to: supply sheath gas to the outer surface of the filter output channel 38; or supply sheath gas to the outer surface of the filter output channel 38 and around the outer surface of the filter output channel 38.

The sheath gas channel 44 may be arranged to: extend to the filter output channel 38 for supplying sheath gas to the outer surface of the filter output channel 38; or extend to the filter output channel 38 and around the filter output channel 38 for supplying sheath gas to the outer surface of the filter output channel 38 and around the outer surface of the filter output channel 38.

The filter 22 may be supported to the filter unit 20 or the housing 26 with the filter output channel 38.

The apparatus 1 may further comprise: a sheath gas source and the sheath gas channel 44 is connected to the sheath gas source for supplying sheath gas into the filter unit 20; or the apparatus 1 further comprises a clean gas source and the sheath gas channel 44 is connected to the clean gas source for supplying sheath gas into the filter unit 20, the clean gas forming the sheath gas; or a clean gas channel 32 and the sheath gas channel 44 is connected to the clean gas channel 32 for supplying sheath gas into the filter unit 20, the clean gas forming the sheath gas.

The clean gas channel 32 may be connected to the clean gas inlet 4 for feeding clean gas into the ionization chamber 6, and that the sheath gas channel 44 is a branch channel of the clean gas channel 32.

The clean gas channel 32 may extend: between the clean gas inlet 4 and the discharge channel 40 for feeding clean gas into the ionization chamber 6; or between the clean gas inlet 4 and the pump 28 for feeding clean gas into the ionization chamber 6.

The clean gas channel 32 may comprise an additional clean gas filter 46; or an additional clean gas filter 46, the additional clean gas filter 46 is arranged in connection with the clean gas channel 32 between the discharge channel 40 and the clean gas inlet 4; or an additional clean gas filter 46, the additional clean gas filter 46 is arranged in connection with the clean gas channel 32 between the discharge channel 40 and the sheath gas channel 44.

The sheath gas channel 44 may be arranged to supply the sheath gas from downstream of the filter 22 to upstream of the filter 22 for filtering the sheath gas; or the sheath gas channel 44 may extend from the downstream of the filter 22 to upstream of the filter 22 for filtering the sheath gas.

Figure 5:
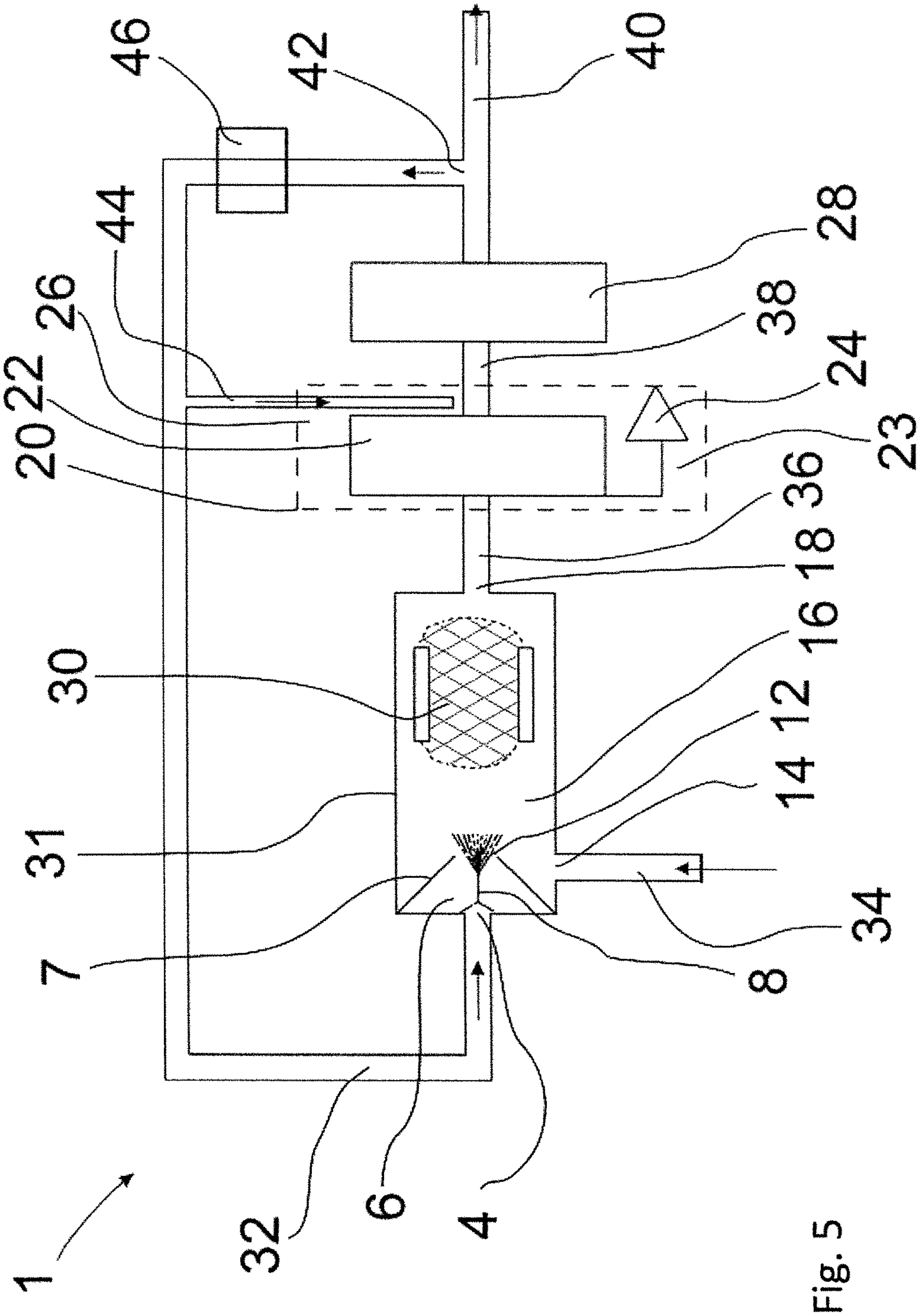
FIG. 5 shows one embodiment of an apparatus for particle measurement according to the present invention.
Figure 6:
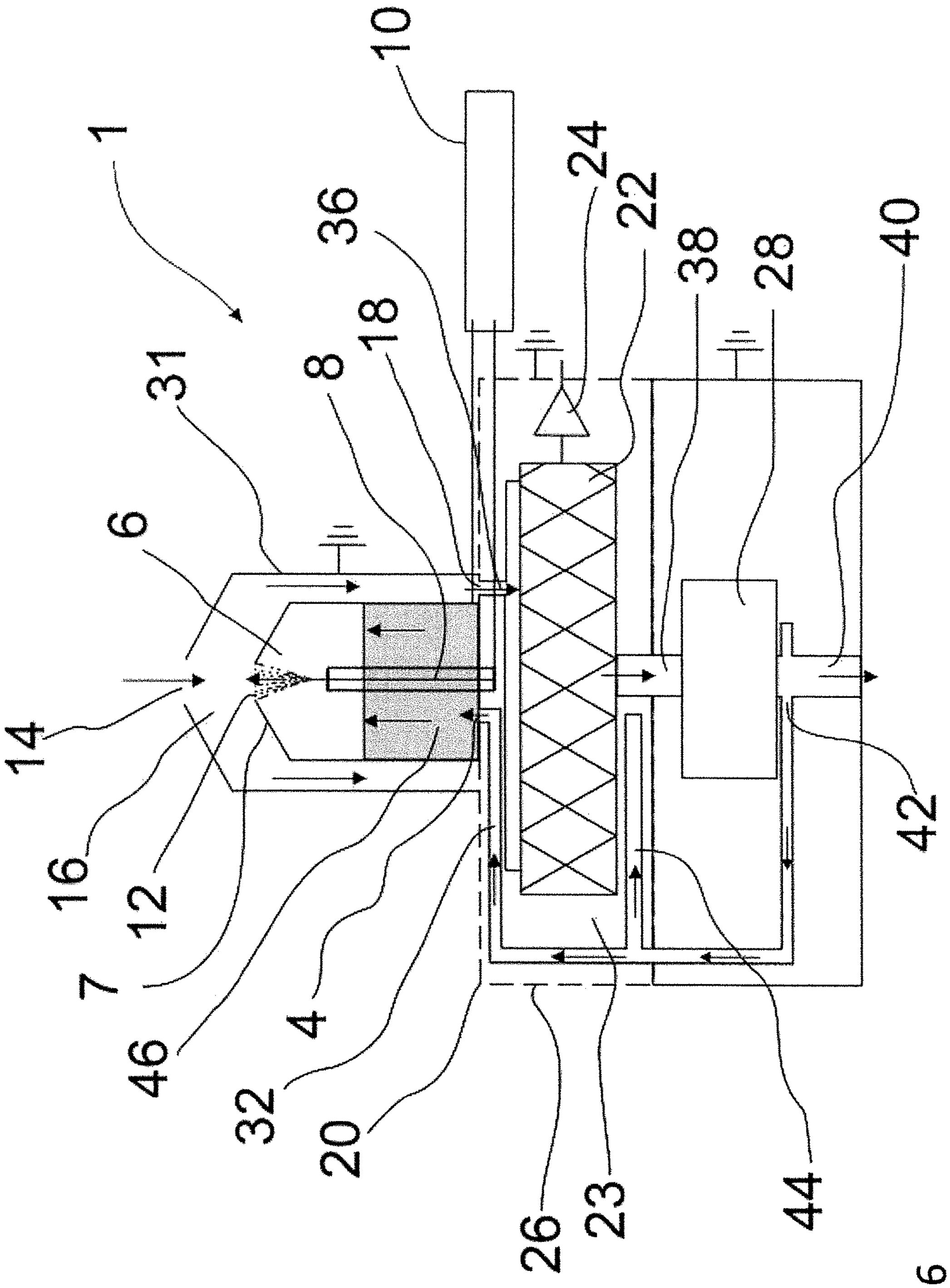
FIG. 6 shows another embodiment of an apparatus for particle measurement according to the present invention.

The following paragraphs relate to FIGS. 5 and 6.

The apparatus of FIGS. 5 and 6 is based idea of providing part of filtered mixed sample aerosol for use as clean gas to the ionizing chamber and discharging only part of the actual filtered mixed sample aerosol.

An advantage of the apparatus according to FIGS. 5 and 6 is that by recirculating the filtered mixed sample aerosol to form the clean gas flow that is to be ionized makes the apparatus more simple and economical without the need to additional filtering and/or providing other sources to bring clean gas to the apparatus.

FIG. 5 shows one embodiment of an apparatus 1 for particle measurement according to the present invention. The clean gas in the context of this application means essentially particle free gas. The apparatus comprises an ionization chamber which comprises a clean gas inlet 4 via which the clean gas is supplied into the ionization chamber 6. The ionization chamber 6 is further provided with an electrical charging element 8 which is arranged to electrically charge the clean gas during or after supplying the clean gas via the clean gas inlet 4 into the ionization chamber. The electrical charging element 8 is connected to charging voltage source (not shown) for providing charging voltage to the electrical charging element. The electrical charging element electrically charges the clean gas as it passes the electrical charging element 8. Thus the ionization chamber provides an ionized clean gas flow into the apparatus.

In other words the ionization chamber 6 comprises a clean gas inlet 4 for feeding clean gas into the ionization chamber 6, a charging element 8 arranged in the ionization chamber 6 for charging the clean gas into ionized clean gas, and an ionized gas outlet 12 for discharging the ionized clean gas from the ionization chamber 6.

In one embodiment of the apparatus 1 the electrical charging element 8 is a corona electrode and the charging voltage source is a corona voltage source.

The apparatus 1 comprises an ionization chamber 6 into which the clean gas is supplied via clean gas channel 32 and the clean gas enters the ionization chamber 6 from the clean gas inlet 4 provided to the ionization chamber 6. The electrical charging element 8 is provided into the ionization chamber 6 such that the clean gas flow passes the electrical charging element 8 as it flows through the ionization chamber 6. The electrical charging element 8, or corona electrode, may be arranged for example to extend inside the ionization chamber 6, as shown in FIG. 5. In one embodiment the electrical charging element 8 may be arranged to extend in the centre of the ionization chamber 6. The electrical charging element 8 may be a rod or a wire which is electrically connected to the charging voltage source. Accordingly, the ionization of the clean gas is carried out in the ionization chamber 6. The ionization chamber 6 further comprises an ionized gas outlet 12 via which the ionized clean gas is discharged from the ionization chamber 6.

The ionization chamber 6 comprises ionization chamber walls 7 defining the ionization chamber 6. The clean gas inlet 4 and the ionized gas outlet 12 may be arranged such that the clean gas flow flows through the ionization chamber 6 passing the electrical charging element 8 between the clean gas inlet 4 and the ionized gas outlet 12. In one embodiment the clean gas inlet 4 and the ionized gas outlet 12 are arranged opposite to each other in the ionization chamber 6 and the electrical charging element 8 is arranged between the clean gas inlet 4 and the ionized gas outlet 12, as shown in FIG. 5. Thus the ionization chamber 6 is provided as a flow-through chamber in which the clean gas flows through the ionization chamber 6 from the clean gas inlet 4 directly to the ionized gas outlet 12. In the embodiment of FIG. 5 the ionization chamber walls 7 are arranged converge towards the ionized gas outlet 12. Thus the ionization chamber 6 tapers towards the ionized gas outlet 12. The ionization chamber 6 therefore may be arranged to taper from the clean gas outlet 4 towards the ionized gas outlet 12 for providing ionized clean gas flow from the ionization chamber 6.

In an alternative embodiment the clean gas inlet 4 and the ionized gas outlet 12 are arranged to the ionization chamber wall 7 transversely or perpendicularly in relation to each other.

In an alternative embodiment the ionization chamber 6 as such may be omitted and the ionization chamber 6 may be arranged in connection with the clean gas channel 32 and at least partly inside the clean gas channel 32, in other words the ionization chamber 6 may be arranged or integrated to the clean gas channel 32. In this case the electrical charging element 8 may be provided to the clean gas channel 32 such that the clean gas is ionized inside the clean gas channel 32 or at the clean gas inlet 4. In this embodiment ionized clean gas in supplied via the clean gas inlet 4.

The apparatus 1 of FIG. 5 further comprises a sample inlet 14 via which sample aerosol flow is supplied into the apparatus 1. The sample aerosol flow is supplied in to the apparatus 1 via sample channel 34 from a space comprising aerosol to be measured with the particle measurement apparatus 1. The space may be a habitable space, industrial space, process chamber, ventilation system, combustion system, exhaust conduit or any other space comprising particle containing aerosol.

The apparatus 1 comprises a mixing chamber 16 in which the ionized clean gas flow and the particle containing sample aerosol flow meet each other and are mixed with each other for providing a mixed sample flow. The mixing chamber 16 is defined by mixing chamber walls 31. The ionized clean gas enters the mixing chamber 16 from the ionized gas outlet 12 and the sample aerosol flow enters the mixing chamber from the sample inlet 14. In the mixing chamber 16 the ionized clean gas flow and the sample aerosol flow collide or mix with each other such that the ionized clean gas electrically charges the particles of the sample aerosol providing a mixed sample flow comprising electrically charged particles. The charging of the particles occurs mainly by diffusion charging such that ions in the ionized clean gas are attached to the particles and the particles become electrically charged.

In the embodiment of FIG. 5 the ionized clean gas enters the mixing chamber 16 from the ionized gas outlet 12 and the sample aerosol flow enters the mixing chamber from the sample inlet 14 transversely to ionized gas outlet 12 and the ionized clean gas flow such that the ionized clean gas flow and the sample aerosol flow collide to each other and becomes mixed. In the embodiment of FIG. 5 the ionized gas outlet 12 is arranged to a first end wall of the mixing chamber 16 and the ionized clean gas enters the mixing chamber 16 in a first flow direction. The sample inlet 14 is arranged to a side wall of the mixing chamber 16 and the sample aerosol flow enters the mixing chamber 16 in a second flow direction transversely or perpendicularly to the first flow direction of the ionized clean gas flow such that the ionized clean gas and the sample aerosol collide and are mixed inside the mixing chamber 16 for electrically charging the particles of the sample aerosol.

In an alternative embodiment the sample inlet 14 may be arranged to the first end wall of the mixing chamber 16 and the ionized gas outlet 12 to the side wall of the mixing chamber 16.

As shown in FIG. 5, the ionization chamber 6 is defined with the ionization chamber walls 7 and provided inside the mixing chamber 16. Thus the ionization chamber 6 is within the mixing chamber 16 and separated with the ionization chamber walls 7. In an alternative embodiment the ionization chamber may be provided upstream and separate of the mixing chamber 16 and the ionized clean gas is transported into the mixing chamber 16 from outside of the mixing chamber 16. In a yet alternative embodiment the ionization chamber 6 is provided to or formed by the clean gas channel 32.

According to the above mentioned the ionization chamber 6 is provided in fluid communication with mixing chamber 16 in all embodiments.

The mixing chamber 16 further comprises a mixing chamber outlet 18 via which the mixed sample flow comprising electrically charged particles is discharged from the mixing chamber 16.

In FIG. 5, the mixing chamber outlet 18 is provided to the second end wall of the mixing chamber 16 opposite the ionized clean gas outlet 12. Therefore, the mixing chamber 16 is provided as a flow-through chamber such that the ionized clean gas flow is directed in the first flow direction towards the mixing chamber outlet 18.

In an alternative embodiment the mixing chamber outlet 18 may be provided to a side wall of the mixing chamber 16. Thus the mixing chamber outlet 18 may be arranged opposite the sample inlet 14 or adjacent the sample inlet 14 or displaced relative to the sample inlet 14. Furthermore, also the sample inlet 14 may be provided to the first end wall of the mixing chamber 16, thus opposite the mixing chamber outlet 18 of FIG. 5.

The mixing chamber 16 is further provided with an ion trap 30 for removing free ions not attached to the particles of the mixed sample aerosol. The ion trap 30 is provided as an ion trap electrode or electrodes having opposite polarity than the free ions. The ion trap electrode may be any kind of electrode, for example such as a plate-like electrode or a net-like electrode. The ion trap electrode may be connected to an ion trap voltage source or it may be grounded such that electric field is provided between the electrical charging element 8 and the ion trap electrode for collecting the free ions not attached to the particles. The ion trap voltage is high enough to deposit the free ions, but due to the lower mobility the electrically charged particles are not deposited to the ion trap electrode.

The ion trap 30 is provided downstream of the ionized gas outlet 12 and the sample inlet 14 such that the ionized clean gas and the sample aerosol are mixed and the particles electrically charged before the mixed sample aerosol meets the ion trap 30 and is subjected to the ion trap voltage. As shown in FIG. 5, the ion trap is provided inside mixing chamber 16 upstream of the mixing chamber outlet 18, or between the ionized gas outlet 12 and the sample inlet 14, and the mixing chamber outlet 18.

In an alternative embodiment the ion trap 30 may be arranged downstream of the mixing chamber 16 and downstream of the mixing chamber outlet 18. Thus in this embodiment the ion trap 30 is separate from the mixing chamber 16.

The apparatus 1 further comprises a filter unit 20 arranged downstream of the mixing chamber 16, as shown in FIG. 5. The filter unit 20 is arranged in fluid communication with the mixing chamber 16 and downstream of the mixing chamber 16. In the embodiment of FIG. 5, the filter unit 20 is connected to the mixing chamber 16 with filter inlet channel 36 for passing the mixed sample aerosol flow from the mixing chamber 16 to the filter unit 20. Therefore, the mixed sample aerosol flow is passed from the mixing chamber 16 via the mixing chamber outlet 18 and the filter inlet channel to the filter unit 20.

It should be noted that the ion trap 30 is provided upstream or before of the filter unit 20. In FIG. 5, the ion trap 30 is provided inside the mixing chamber 16. In an alternative embodiment the ion trap 30 may also be provided to the filter inlet channel 36 between the mixing chamber 16 and the filter unit 20.

The filter unit 20 comprises a housing 26 inside which a filter 22 is arranged. The housing 20 comprises or is formed as a faraday cage for electrically separating the filter unit 20 from the other parts of the apparatus 1, and especially from the ionization chamber 6, electrical charging element 8, ion trap 30 and the mixing chamber 16. The filter unit 20 further comprises an electrical insulator 23 inside the housing 20. The filter 22 is embedded inside the insulator 23 for further electrically insulating the filter 22 from the other parts of the apparatus 1. The filter 22 may be any kind of conventional filter, such as a carbon filter or a HEPA filter or some other kind of a filter. The structure of the filter unit is arranged such that the filter 22 may be removed from the filter unit 20 and replaced or changed to a new filter 22.

The electrically charged particles of the mixed sample aerosol are filtered and removed from the mixed sample aerosol flow in the filter 22. During the filtration with the filter 22 the electrically charged particles are deposited to the filter 22 and accumulated to the filter 22.

As the electrically charged particles are deposited to the filter 22 they generate electrical current to the filter 22. The filter unit 20 therefore further comprises electrical measurement element 24 connected to the filter 22. The electrical measurement element 24 is arranged to measure the electrical current produced by the electrically charged particles in the filter 22 as they are deposited to the filter 22. The electrical measurement element 22 provides an output signal based on the measurement results of the electrical current measurements from the filter 22. The output signal may be transmitted to a process unit (not shown) for further analysis. The electrical measurement element 24 may comprise an electrometer or the like measuring device.

The ion trap 30 has to be arranged upstream of or before the filter unit 20 such that the free ions present in the mixed sample aerosol do not affect the particle measurement based on the measuring the electrical current carried by the electrically charged particles.

In the filter unit 20 the electrically charged particles are filtered from the mixed sample aerosol and a filtered mixed sample aerosol flow is discharged from the filter unit 20.

Downstream of the filter unit 20 is provided a pump 28 or other kind of suction device. The pump 28 is arranged in fluid communication with the filter unit 20 and arranged downstream of the filter unit 20. The pump 28 is arranged to generate flow of at least sample aerosol, mixed sample aerosol and filtered mixed sample aerosol through the apparatus 1. The pump 28 may also be arranged to generate flow of the clean gas and ionized clean gas into or in the apparatus 1.

The pump 28 is connected to the filter unit 20 with a filter output channel 38 extending between the filter unit 20 and the pump 28 for passing the filtered mixed sample aerosol from the filter unit 20 to the pump 28. The filtered mixed sample aerosol is discharged from the pump 28 and from the apparatus 1 via discharge channel 40. The filtered mixed sample aerosol may be discharged via the discharge channel 40 out of the apparatus to environment or back to the space from where it was taken.

According to the invention the clean gas inlet 4 is in fluid communication with the discharge channel 40 for providing clean gas to the ionization chamber 6. This means that part of the filtered mixed sample aerosol forms the clean gas supplied through the clean gas channel 32 to the clean gas inlet 4 to be fed into the ionization chamber 6. As FIG. 5 shows in one embodiment of the invention the clean gas intake 42 is arranged in the discharge channel 40 and the clean gas channel 32 extends from the clean gas intake 42 as a side channel to the discharge channel 40 being the main channel. In another embodiment of the invention the clean gas channel 32 may be arranged to extend from the pump 28 as a separate channel from the discharge channel 40 but still delivering the same filtered mixed sample aerosol through the clean gas channel 32 to the clean gas inlet 4. If needed an additional clean gas filter 46 may be arranged in the clean gas channel 32.

So the apparatus 1 according to the invention comprises a clean gas channel 32 arranged to extend between the discharge channel 40 and the ionization chamber 6. In one embodiment of the invention the discharge channel 40 comprises a clean gas intake 42 for forming a fluid connection to the clean gas channel 32 from the discharge channel 40. This embodiment is shown in FIG. 5. The apparatus comprises a clean gas channel 32 arranged to extend between the pump 28 and the ionization chamber 6. As described the clean gas channel 32 may extend between the pump 28 and the ionization chamber 6 such that it diverges from the discharge channel 40 with a clean gas intake 42. Another embodiment of it is that the clean gas channel 32 is arranged to extend between the pump 28 and the ionization chamber 6 as a separate channel from the discharge channel 40.

FIG. 6 shows another embodiment of an apparatus 1 for particle measurement according to the present invention. It should be noted that construction of the apparatus of FIG. 6 is different from the construction of apparatus of FIG. 5, but similar parts are denoted with same reference numerals. Furthermore, the same principles of operation and purpose of different parts apply to both embodiment of the apparatus and also to other possible modifications of the apparatus according to the present invention.

The apparatus 1 of FIG. 6 comprises an ionization chamber 6 comprising a clean gas inlet 4 for feeding clean gas into the ionization chamber 6, a charging element 8 arranged in the ionization chamber 6 for charging the clean gas into ionized clean gas, and an ionized gas outlet 12 for discharging the ionized clean gas from the ionization chamber 6. The clean gas in the context of this application means essentially particle free gas. The ionization chamber 6 comprises a clean gas inlet 4 via which the clean gas is supplied into the ionization chamber 6. The ionization chamber 6 is further provided with an electrical charging element 8 which is arranged to electrically charge the clean gas during or after supplying the clean gas via the clean gas inlet 4 into the apparatus 1. The electrical charging element 8 is connected to charging voltage source 10 for providing charging voltage to the electrical charging element 8. The charging voltage source 10 may be any kind voltage source, such as high voltage source. The electrical charging element 8 electrically charges the clean gas as it passes the electrical charging element 8. Thus the ionization chamber 6 provides an ionized clean gas flow into the apparatus 1.

In one embodiment of the apparatus 1 of FIG. 6 the electrical charging element 8 is a corona electrode and the charging voltage source 10 is a corona voltage source.

The apparatus 1 comprises an ionization chamber 6 into which the clean gas is supplied via clean gas channel 32 and the clean gas enters the ionization chamber 6 from the clean gas inlet 4 provided to the ionization chamber 6. The electrical charging element 8 is provided into the ionization chamber 6 such that the clean gas flow passes the electrical charging element 8 as it flows through the ionization chamber 6. The electrical charging element 8, or corona electrode, may be arranged for example to extend inside the charging chamber 6, as shown in FIG. 6. In one embodiment the electrical charging element 8 may be arranged to extend in the centre of the ionization chamber 6. The electrical charging element 8 may be a rod or wire which is electrically connected to the charging voltage source. Accordingly, the ionization of the clean gas is carried out in the ionization chamber 6. The ionization chamber 6 further comprises an ionized gas outlet 12 via which the ionized clean gas is discharged from the ionization chamber 6.

The ionization chamber 6 comprises chamber walls 7 defining the ionization chamber 6. The clean gas inlet 4 and the ionized gas outlet 12 may be arranged such that the clean gas flows through the ionization chamber 6 passing the electrical charging element 8 between the clean gas inlet 4 and the ionized gas outlet 12. In one embodiment the clean gas inlet 4 and the ionized gas outlet 12 are arranged opposite each other in the ionization chamber 6 and the electrical charging element 8 is arranged between the clean gas inlet 4 and the ionized gas outlet 12, as shown in FIG. 6. Thus the ionization chamber is provided as flow-through chamber in which the clean gas flows through the ionization chamber 6 from the clean gas inlet 4 directly to the ionized gas outlet 12. In the embodiment of the apparatus of FIG. 5 the ionization chamber walls 7 are arranged converge towards the ionized gas outlet 12. Thus the ionization chamber 6 tapers towards the ionized gas outlet 12. The ionization chamber 6 therefore may be arranged to taper from the clean gas outlet 4 towards the ionized gas outlet 12 for providing ionized clean gas flow from the ionization chamber 6.

In an alternative embodiment the clean gas inlet 4 and the ionized gas outlet 12 are arranged to the ionization chamber wall 7 transversely or perpendicularly in relation to each other.

In an alternative embodiment the ionization chamber 6 as such may be omitted and the ionization chamber 6 may be arranged or integrated to the clean gas channel 32. In this case the electrical charging element 8 may be provided to the clean gas channel 32 such that the clean gas is ionized inside the clean gas channel 32 or at the clean gas inlet 4. In this embodiment ionized clean gas in supplied via the clean gas inlet 4.

The apparatus 1 further comprises a sample inlet 14 via which sample aerosol flow is supplied into the apparatus. The sample aerosol flow is supplied into the apparatus a space comprising aerosol to be measured with the particle measurement apparatus 1. The space may be a habitable space, industrial space, process chamber, ventilation system, combustion system, exhaust conduit or any other space comprising particle containing aerosol.

The apparatus 1 comprises a mixing chamber 16 in which the ionized clean gas flow and the particle containing sample aerosol flow meet each other and are mixed with each other for providing a mixed sample flow. The mixing chamber 16 is defined by mixing chamber walls 31. The ionized clean gas enters the mixing chamber 16 from the ionized gas outlet 12 and the sample aerosol flow enters the mixing chamber from the sample inlet 14. In the mixing chamber 16 the ionized clean gas flow and the sample aerosol flow collide and mix with each other such that the ionized clean gas electrically charges the particles of the sample aerosol providing a mixed sample aerosol comprising electrically charged particles. The charging of the particles occurs mainly by diffusion charging such that ions in the ionized clean gas are attached to the particles and the particles become electrically charged.

In the embodiment of FIG. 6 the ionized clean gas enters the mixing chamber 16 from the ionized gas outlet 12 and the sample aerosol flow enters the mixing chamber 16 from the sample inlet 14 opposite the ionized gas outlet 12 and ionized clean gas flow such that the ionized clean gas flow and the sample aerosol flow collide to each other and becomes mixed. In the embodiment of FIG. 6 the ionized gas outlet 12 is arranged towards and opposite the sample inlet 14 and the ionized clean gas enters the mixing chamber 16 in a first flow direction. The sample inlet 14 is arranged towards and opposite the ionized gas outlet 12 and the sample aerosol flow enters the mixing chamber 16 in a second flow direction opposite the first flow direction of the ionized clean gas flow such that the ionized clean gas and the sample aerosol collide directly against each other and are mixed inside the mixing chamber 16 for electrically charging the particles of the sample aerosol. In other words, arranging the ionized gas outlet 12 and the sample inlet 14 opposite each other provides counter current flow of the ionized clean gas and the sample aerosol inside the mixing chamber 16. Thus the ionized clean gas and the sample aerosol may collide directly against each other in a collision angle of substantially 180 degrees.

As shown in FIG. 6, the ionization chamber 6 is defined with the ionization chamber walls 7 and provided inside the mixing chamber 16. Thus the ionization chamber 6 is within the mixing chamber 16 and separated with the ionization chamber walls 7. The mixing chamber 16 and the mixing chamber walls 31 surround the ionization chamber 6. Therefore the ionization chamber 6 is nested inside the mixing chamber 16. There is gap between the ionization chamber walls 7 and the mixing chamber walls 31, as shown in FIG. 6, for providing a flow path for the mixed sample aerosol flow comprising electrically charged particles.

In an alternative embodiment the ionization chamber may be provided outside of the mixing chamber 16 and the ionized clean gas in transported into the mixing chamber from outside of the mixing chamber 16. In a yet alternative embodiment the ionization chamber 6 is provided to or formed by the clean gas channel 32.

According to the above mentioned the ionization chamber 6 is provided in fluid communication with mixing chamber 16 in all embodiments of the apparatus according to the FIG. 6.

The mixing chamber 16 further comprises mixing chamber outlet 18 via which the mixed sample aerosol comprising electrically charged particles is dis-charged from the mixing chamber 16. The mixed sample aerosol flows from the flow path between the ionization chamber walls 7 and the mixing chamber walls 31 to mixing chamber outlet 18 and discharges from the mixing chamber 16.

In FIG. 6, the sample inlet 14 is provided to a first end or first end wall of the mixing chamber 16 and the mixing chamber outlet 18 is provided to a second end or second end wall of the mixing chamber 16 opposite the sample inlet 14. Therefore, the mixing chamber 16 is provided as flow-through chamber such that the sample aerosol flows through the mixing chamber 16 and directed in the second flow direction towards the mixing chamber outlet 18.

In an alternative embodiment the mixing chamber outlet 18 may be provided to a side wall of the mixing chamber 16 transversely or perpendicularly to the sample inlet 14.

The mixing chamber 16 is further provided with ion trap 30 for removing free ions not attached to the particles of the mixed sample aerosol. In the embodiment of FIG. 6 the ion trap is provided by the mixing chamber walls 31. Thus the mixing chamber walls 31 forms the ion trap or an ion trap electrode. As shown in FIG. 6, the charging voltage source 10 is electrically connected to the electrical charging element 8 and to the ionization chamber walls 7. Thus the electrical charging element 8 and the ionization chamber walls 7 are at same electrical potential. The mixing chamber walls 31 are grounded such that the mixing chamber walls 31 form the ion trap electrode for collecting and removing free ions from the mixed sample aerosol as the mixed sample aerosol passes the mixing chamber walls 31 between the ionization chamber 6 and the mixing chamber 16. Therefore, an electric field is provided between the ionization chamber walls 7 and the mixing chamber walls 31.

The ion trap, or the mixing chamber walls 31, is thus provided as an ion trap electrode or electrodes having opposite polarity than the free ions. Alternative the mixing chamber 16 may be provided with separate electrode or electrodes formed as ion trap electrodes. The separate ion trap electrode may be any kind of electrode, for example such as plate-like electrode or net-like electrode. The ion trap electrode may also be connected to an ion trap voltage source or it may be grounded such that electric field is provided between the electrical charging element 8 and the ionization chamber wall 7, and the ion trap electrode for collecting the free ions not attached to the particles. The ion trap voltage is high enough to deposit the free ions, but due to the lower mobility the electrically charged particles are not deposited to the ion trap electrode.

The ion trap is provided such that the ionized clean gas and the sample aerosol are mixed and the particles electrically charged before the mixed sample aerosol meets the ion trap and is subjected to the ion trap voltage.

In an alternative embodiment the ion trap may be arranged downstream of the mixing chamber 16 and downstream of the mixing chamber outlet 18. Thus in this embodiment the ion trap is separate from the mixing chamber 16.

The apparatus 1 further comprises a filter unit 20 arranged downstream of the mixing chamber 16, as shown in FIG. 6. The filter unit 20 is arranged in fluid communication with the mixing chamber 16 and downstream of the mixing chamber 16. In the embodiment of FIG. 6, the filter unit 20 is connected to the mixing chamber 16 with filter inlet channel 36 for passing the mixed sample aerosol flow from the mixing chamber 16 to the filter unit 20. Therefore, the mixed sample aerosol flow is passed from the mixing chamber 16 via the mixing chamber outlet 18 and the filter inlet channel 36 to the filter unit 20.

It should be noted that the ion trap 30 is provided upstream or before of the filter unit 20. In FIG. 5, the ion trap 30 is provided inside the mixing chamber 16. In an alternative embodiment the ion trap 30 may also be provided to the filter inlet channel 36 between the mixing chamber 16 and the filter unit 20.

The filter unit 20 comprises a housing 26 inside which a filter 22 is arranged. The housing 20 comprises or is formed as a faraday cage for electrically separating the filter unit 20 from the other parts of the apparatus 1, and especially from the ionization chamber 6, electrical charging element 8, ion trap and the mixing chamber 16. The filter unit 20 further comprises an electrical insulator 23 inside the housing 20. The filter 22 is embedded inside the insulator 23 for further electrically insulating the filter 22 from the other parts of the apparatus 1. The filter 22 may be any kind of conventional filter, such as carbon filter or HEPA filter or some other kind of filter. The structure of the filter unit 20 is arranged such that the filter 22 may be removed from the filter unit 20 and replaced or changed to a new filter 22.

The electrically charged particles of the mixed sample aerosol are filtered and removed from the mixed sample aerosol in the filter 22. During the filtration with the filter 22 the electrically charged particles are deposited to the filter 22 and accumulate to the filter 22.

As the electrically charged particles are deposited to the filter 22 they generate electrical current to the filter 22. The filter unit 20 therefore further comprises electrical measurement element 24 connected to the filter 22. The electrical measurement element 24 is arranged to measure the electrical current produced by the electrically charged particles in the filter 22 as they are deposited to the filter 22. The electrical measurement element 22 provides an output signal based on the measurement results of the electrical current measurements from the filter 22. The output signal may be transmitted to a process unit (not shown) for further analysis. The electrical measurement element 24 may comprise an electrometer or the like measuring device.

The ion trap has to be arranged upstream of or before the filter unit 20 such that the free ions present invention mixed sample aerosol do not affect the particle measurement based on the measuring the electrical current carried by the electrically charged particles.

In the filter unit 20 the electrically charged particles are filtered from the mixed sample aerosol and a filtered mixed sample aerosol flow is discharged from the filter unit 20.

Downstream of the filter unit 20 is provided a pump 28 or other kind of suction device. The pump 28 is arranged in fluid communication with the filter unit 20 and arranged downstream of the filter unit 20. The pump 28 is arranged to generate flow of at least sample aerosol, mixed sample aerosol and filtered mixed sample aerosol through the apparatus 1. The pump 28 may also be arranged to generate flow of the clean gas and ionized clean gas into or in the apparatus 1.

The pump 28 is connected to the filter unit 20 with a filter output channel 38 extending between the filter unit 20 and the pump 28 for passing the filtered mixed sample aerosol from the filter unit 20 to the pump 28. The filtered mixed sample aerosol is discharged from the pump 28 and from the apparatus 1 via discharge channel 40. The filtered mixed sample aerosol may be discharged via the discharge channel 40 out of the apparatus 1 to environment or back to the space from where it was taken.

As shown in FIG. 6 the discharge channel 40 discharges the filtered mixed sample aerosol out from the apparatus 1. The discharge channel 40 comprises in this embodiment of the invention a clean gas intake 42 for feeding filtered mixed sample aerosol as a clean gas toward the ionization chamber 6. The clean gas intake 42 provides an opening for the clean gas channel 32. The embodiment of the invention shown in FIG. 6 does not have any additional clean gas filters in the clean gas channel 32 but instead the additional clean gas filter is arranged in connection with the ionization chamber 6 and the clean gas inlet 4 such that the clean gas supplied from the clean gas inlet 4 is fed through the additional clean gas filter 46 before being ionized in the ionization chamber 6.

According to the above mentioned and FIGS. 5 and 6, the apparatus 1 may comprise: an ionization chamber 6 comprising a clean gas inlet 4 for feeding clean gas into the ionization chamber 6, a charging element 8 arranged in the ionization chamber 6 for charging the clean gas into ionized clean gas, and an ionized gas outlet 12 for discharging the ionized clean gas from the ionization chamber 6; a mixing chamber 16 comprising a sample inlet 14 for feeding sample aerosol into the mixing chamber 16, said mixing chamber 16 is in a fluid communication with the ionization chamber 6 for feeding ionized clean gas from the ionization chamber 6 into the mixing chamber 16, and a mixing chamber outlet 18 for discharging mixed sample aerosol formed in the mixing chamber 16 by mixing ionized clean gas and sample aerosol, said mixed sample aerosol comprising electrically charged particles; an ion trap 30 for removing ions not attached to particles from the mixed sample aerosol; a filter unit 20 for filtering electrically charged particles from the mixed sample aerosol for forming filtered mixed sample aerosol, said filter unit 20 comprising a filter 22 and a housing 26, said filter unit 20 is in fluid communication with the mixing chamber 16 and arranged downstream of the mixing chamber 16; a pump 28 for generating flow of clean gas, ionized clean gas, sample aerosol, mixed sample aerosol and filtered mixed sample aerosol, said pump 28 is in fluid communication with the filter unit 20 and arranged downstream of the filter unit 20; and a discharge channel 40 connected to the pump 28 for discharging filtered mixed sample aerosol from the apparatus 1; the clean gas inlet 4 is in fluid communication with the discharge channel 40 for providing clean gas to the ionization chamber 6.

The apparatus 1 may further comprise a clean gas channel 32 arranged to extend between the discharge channel 40 and the ionization chamber 6.

The discharge channel 40 may comprise a clean gas intake 42 for forming a fluid connection to the clean gas channel 32 from the discharge channel 40.

The apparatus further may comprise a clean gas channel 32 arranged to extend between the pump 28 and the ionization chamber 6.

The clean gas channel 32 may comprise an additional clean gas filter 46. The additional clean gas filter 46 may be arranged in connection with the clean gas channel 32 such that clean gas supplied through the clean gas channel 32 is fed through the additional clean gas filter 46 before being ionized in the ionization chamber 6.

The ion trap 30 may be arranged in the mixing chamber 16. Furthermore, the ion trap 30 may be arranged to a side wall 31 of the mixing chamber 16, or the ion trap 30 may be arranged downstream of the mixing chamber 16 before the filter unit 20.

The ionization chamber 6 may be arranged in connection with the clean gas channel 32 and at least partly inside the clean gas channel 32, or the ionization chamber 6 may be arranged at least partly within the mixing chamber 16.

A filter inlet channel 36 may be arranged between the mixing chamber 16 and the filter 22 for feeding the mixed sample aerosol to the filter 22. Also a filter output channel 38 is arranged between the filter 22 and the pump 28 for feeding the filtered mixed sample aerosol.

The filter unit 20 may further comprise an electrical measurement element 24 for measuring the electrical current produced by the electrically charged particles in the filter 22 as they are deposited to the filter 22.

The apparatus 1 may further comprise an additional clean gas filter 46 arranged in connection with the ionization chamber 6.

Figure 7:
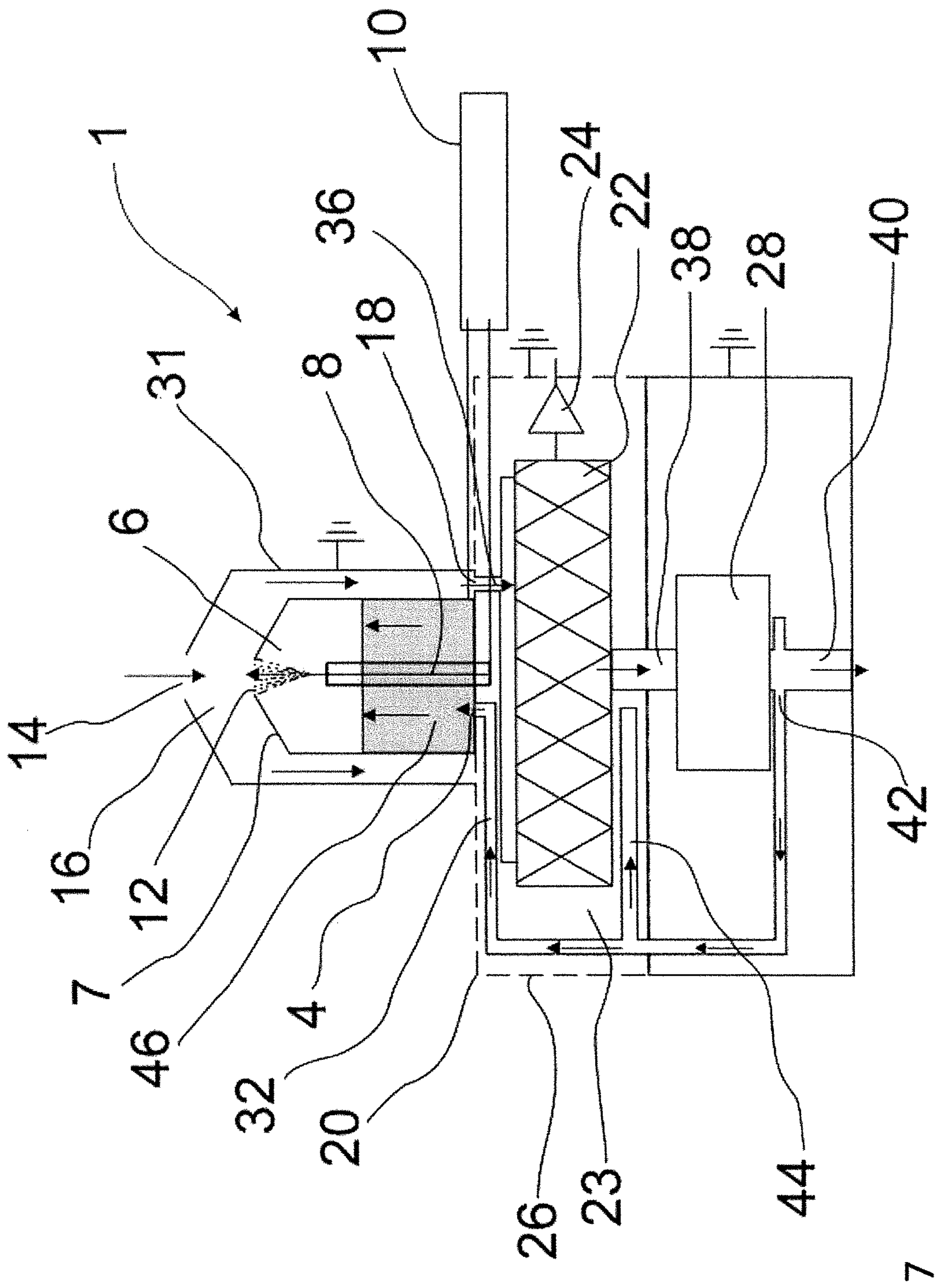
FIG. 7 shows an apparatus for particle measurement according to the present invention.
Figure 8:
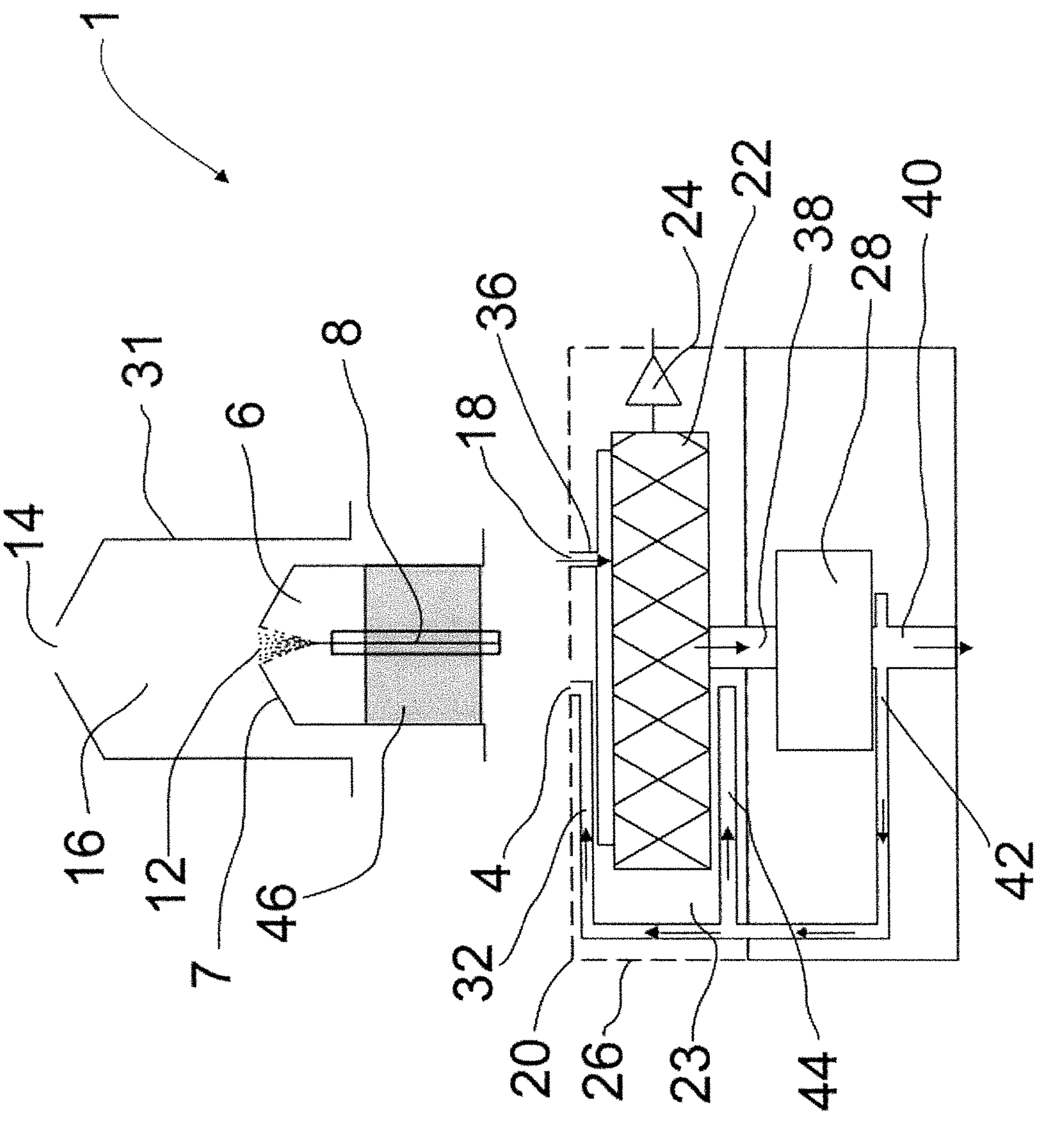
FIG. 8 shows one embodiment of an apparatus for particle measurement according to the present invention.
Figure 9:
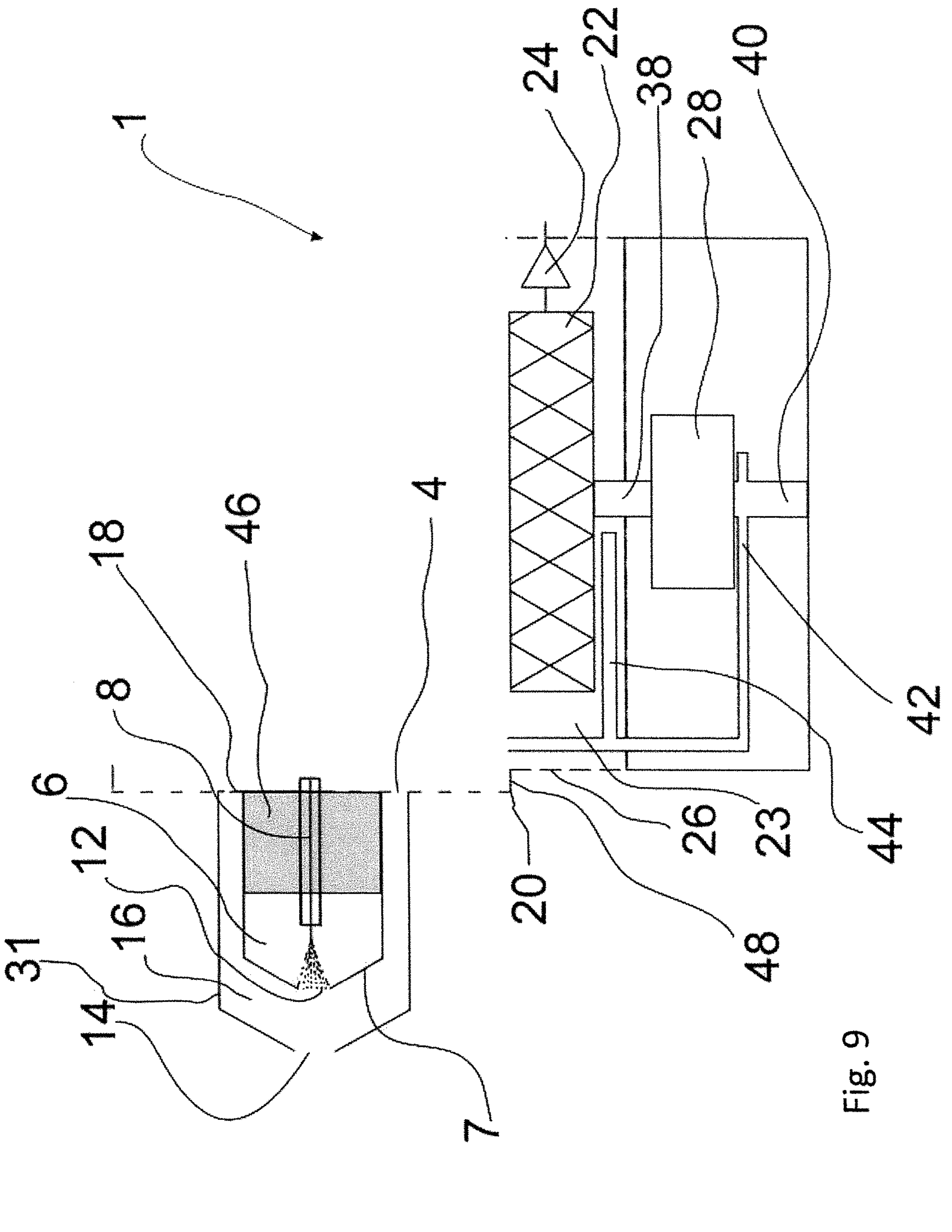
FIG. 9 shows another embodiment of an apparatus for particle measurement according to the present invention.

The following paragraphs relate to FIGS. 7, 8 and 9.

The apparatus of FIGS. 7, 8 and 9 is based on the idea of providing an apparatus for particle measurement having a stacked structure. Further idea is that the different flows inside the apparatus are essentially counter flow type flows, i.e. the flows moving essentially in two directions from top to down and down to top or from one side to another side and back. This means that the flow directions do not spread all over the apparatus but the channels guiding the flows are mainly parallel.

An advantage of the apparatus according to the present invention is that the apparatus is easily cleaned and maintained because the mixing chamber and the ionization chamber are easily extracted and ion source can be changed as one component. The filter is also easily change by splitting the stack of the apparatus.

FIG. 7 shows another embodiment of an apparatus 1 for particle measurement according to the present invention. It should be noted that construction of the apparatus of FIG. 7 is different from the construction of apparatus of FIG. 7, but similar parts are denoted with same reference numerals. Furthermore, the same principles of operation and purpose of different parts apply to both embodiment of the apparatus and also to other possible modifications of the apparatus according to the present invention.

The apparatus 1 of FIG. 7 comprises an ionization chamber 6 comprising a clean gas inlet 4 for feeding clean gas into the ionization chamber 6, a charging element 8 arranged in the ionization chamber 6 for charging the clean gas into ionized clean gas, and an ionized gas outlet 12 for discharging the ionized clean gas from the ionization chamber 6. The clean gas in the context of this application means essentially particle free gas. The ionization chamber 6 comprises a clean gas inlet 4 via which the clean gas is supplied into the ionization chamber 6. The ionization chamber 6 is further provided with an electrical charging element 8 which is arranged to electrically charge the clean gas during or after supplying the clean gas via the clean gas inlet 4 into the apparatus 1. The electrical charging element 8 is connected to charging voltage source 10 for providing charging voltage to the electrical charging element 8. The charging voltage source 10 may be any kind voltage source, such as high voltage source. The electrical charging element 8 electrically charges the clean gas as it passes the electrical charging element 8. Thus the ionization chamber 6 provides an ionized clean gas flow into the apparatus 1.

In one embodiment of the apparatus 1 of FIG. 7 the electrical charging element 8 is a corona electrode and the charging voltage source 10 is a corona voltage source.

The apparatus 1 comprises an ionization chamber 6 into which the clean gas is supplied via clean gas channel 32 and the clean gas enters the ionization chamber 6 from the clean gas inlet 4 provided to the ionization chamber 6. The electrical charging element 8 is provided into the ionization chamber 6 such that the clean gas flow passes the electrical charging element 8 as it flows through the ionization chamber 6. The electrical charging element 8, or corona electrode, may be arranged for example to extend inside the charging chamber 6, as shown in FIG. 7. In one embodiment the electrical charging element 8 may be arranged to extend in the centre of the ionization chamber 6. The electrical charging element 8 may be a rod or wire which is electrically connected to the charging voltage source. Accordingly, the ionization of the clean gas is carried out in the ionization chamber 6. The ionization chamber 6 further comprises an ionized gas outlet 12 via which the ionized clean gas is discharged from the ionization chamber 6.

The ionization chamber 6 comprises chamber walls 7 defining the ionization chamber 6. The clean gas inlet 4 and the ionized gas outlet 12 may be arranged such that the clean gas flows through the ionization chamber 6 passing the electrical charging element 8 between the clean gas inlet 4 and the ionized gas outlet 12. In one embodiment the clean gas inlet 4 and the ionized gas outlet 12 are arranged opposite each other in the ionization chamber 6 and the electrical charging element 8 is arranged between the clean gas inlet 4 and the ionized gas outlet 12, as shown in FIG. 7. Thus the ionization chamber is provided as flow-through chamber in which the clean gas flows through the ionization chamber 6 from the clean gas inlet 4 directly to the ionized gas outlet 12. In the embodiment of the apparatus of FIG. 7 the ionization chamber walls 7 are arranged converge towards the ionized gas outlet 12. Thus the ionization chamber 6 tapers towards the ionized gas outlet 12. The ionization chamber 6 therefore may be arranged to taper from the clean gas outlet 4 towards the ionized gas outlet 12 for providing ionized clean gas flow from the ionization chamber 6.

In an alternative embodiment the clean gas inlet 4 and the ionized gas outlet 12 are arranged to the ionization chamber wall 7 transversely or perpendicularly in relation to each other.

In an alternative embodiment the ionization chamber 6 as such may be omitted and the ionization chamber 6 may be arranged or integrated to the clean gas channel 32. In this case the electrical charging element 8 may be provided to the clean gas channel 32 such that the clean gas is ionized inside the clean gas channel 32 or at the clean gas inlet 4. In this embodiment ionized clean gas in supplied via the clean gas inlet 4.

The apparatus 1 further comprises a sample inlet 14 via which sample aerosol flow is supplied into the apparatus. The sample aerosol flow is supplied into the apparatus a space comprising aerosol to be measured with the particle measurement apparatus 1. The space may be a habitable space, industrial space, process chamber, ventilation system, combustion system, exhaust conduit or any other space comprising particle containing aerosol.

The apparatus 1 comprises a mixing chamber 16 in which the ionized clean gas flow and the particle containing sample aerosol flow meet each other and are mixed with each other for providing a mixed sample flow. The mixing chamber 16 is defined by mixing chamber walls 31. The ionized clean gas enters the mixing chamber 16 from the ionized gas outlet 12 and the sample aerosol flow enters the mixing chamber from the sample inlet 14. In the mixing chamber 16 the ionized clean gas flow and the sample aerosol flow collide and mix with each other such that the ionized clean gas electrically charges the particles of the sample aerosol providing a mixed sample aerosol comprising electrically charged particles. The charging of the particles occurs mainly by diffusion charging such that ions in the ionized clean gas are attached to the particles and the particles become electrically charged.

In the embodiment of FIG. 7 the ionized clean gas enters the mixing chamber 16 from the ionized gas outlet 12 and the sample aerosol flow enters the mixing chamber 16 from the sample inlet 14 opposite the ionized gas outlet 12 and ionized clean gas flow such that the ionized clean gas flow and the sample aerosol flow collide to each other and becomes mixed. In the embodiment of FIG. 7 the ionized gas outlet 12 is arranged towards and opposite the sample inlet 14 and the ionized clean gas enters the mixing chamber 16 in a first flow direction. The sample inlet 14 is arranged towards and opposite the ionized gas outlet 12 and the sample aerosol flow enters the mixing chamber 16 in a second flow direction opposite the first flow direction of the ionized clean gas flow such that the ionized clean gas and the sample aerosol collide directly against each other and are mixed inside the mixing chamber 16 for electrically charging the particles of the sample aerosol. In other words, arranging the ionized gas outlet 12 and the sample inlet 14 opposite each other provides counter current flow of the ionized clean gas and the sample aerosol inside the mixing chamber 16. Thus the ionized clean gas and the sample aerosol may collide directly against each other in a collision angle of substantially 180 degrees.

As shown in FIG. 7, the ionization chamber 6 is defined with the ionization chamber walls 7 and provided inside the mixing chamber 16. Thus the ionization chamber 6 is within the mixing chamber 16 and separated with the ionization chamber walls 7. The mixing chamber 16 and the mixing chamber walls 31 surround the ionization chamber 6. Therefore the ionization chamber 6 is nested inside the mixing chamber 16. There is gap between the ionization chamber walls 7 and the mixing chamber walls 31, as shown in FIG. 7, for providing a flow path for the mixed sample aerosol flow comprising electrically charged particles.

In an alternative embodiment the ionization chamber may be provided outside of the mixing chamber 16 and the ionized clean gas in transported into the mixing chamber from outside of the mixing chamber 16. In a yet alternative embodiment the ionization chamber 6 is provided to or formed by the clean gas channel 32.

According to the above mentioned the ionization chamber 6 is provided in fluid communication with mixing chamber 16 in all embodiments of the apparatus according to the FIG. 7.

The mixing chamber 16 further comprises mixing chamber outlet 18 via which the mixed sample aerosol comprising electrically charged particles is dis-charged from the mixing chamber 16. The mixed sample aerosol flows from the flow path between the ionization chamber walls 7 and the mixing chamber walls 31 to mixing chamber outlet 18 and discharges from the mixing chamber 16.

In FIG. 7, the sample inlet 14 is provided to a first end or first end wall of the mixing chamber 16 and the mixing chamber outlet 18 is provided to a second end or second end wall of the mixing chamber 16 opposite the sample inlet 14. Therefore, the mixing chamber 16 is provided as flow-through chamber such that the sample aerosol flows through the mixing chamber 16 and directed in the second flow direction towards the mixing chamber outlet 18.

In an alternative embodiment the mixing chamber outlet 18 may be provided to a side wall of the mixing chamber 16 transversely or perpendicularly to the sample inlet 14.

The mixing chamber 16 is further provided with ion trap 30 for removing free ions not attached to the particles of the mixed sample aerosol. In the embodiment of FIG. 7 the ion trap is provided by the mixing chamber walls 31. Thus the mixing chamber walls 31 forms the ion trap or an ion trap electrode. As shown in FIG. 7, the charging voltage source 10 is electrically connected to the electrical charging element 8 and to the ionization chamber walls 7. Thus the electrical charging element 8 and the ionization chamber walls 7 are at same electrical potential. The mixing chamber walls 31 are grounded such that the mixing chamber walls 31 form the ion trap electrode for collecting and removing free ions from the mixed sample aerosol as the mixed sample aerosol passes the mixing chamber walls 31 between the ionization chamber 6 and the mixing chamber 16. Therefore, an electric field is provided between the ionization chamber walls 7 and the mixing chamber walls 31.

The ion trap, or the mixing chamber walls 31, is thus provided as an ion trap electrode or electrodes having opposite polarity than the free ions. Alternative the mixing chamber 16 may be provided with separate electrode or electrodes formed as ion trap electrodes. The separate ion trap electrode may be any kind of electrode, for example such as plate-like electrode or net-like electrode. The ion trap electrode may also be connected to an ion trap voltage source or it may be grounded such that electric field is provided between the electrical charging element 8 and the ionization chamber wall 7, and the ion trap electrode for collecting the free ions not attached to the particles. The ion trap voltage is high enough to deposit the free ions, but due to the lower mobility the electrically charged particles are not deposited to the ion trap electrode.

The ion trap is provided such that the ionized clean gas and the sample aerosol are mixed and the particles electrically charged before the mixed sample aerosol meets the ion trap and is subjected to the ion trap voltage.

In an alternative embodiment the ion trap may be arranged downstream of the mixing chamber 16 and downstream of the mixing chamber outlet 18. Thus in this embodiment the ion trap is separate from the mixing chamber 16.

The apparatus 1 further comprises a filter unit 20 arranged downstream of the mixing chamber 16, as shown in FIG. 7. The filter unit 20 is arranged in fluid communication with the mixing chamber 16 and downstream of the mixing chamber 16. In the embodiment of FIG. 7, the filter unit 20 is connected to the mixing chamber 16 with filter inlet channel 36 for passing the mixed sample aerosol flow from the mixing chamber 16 to the filter unit 20. Therefore, the mixed sample aerosol flow is passed from the mixing chamber 16 via the mixing chamber outlet 18 and the filter inlet channel 36 to the filter unit 20.

It should be noted that the ion trap 30 is provided upstream or before of the filter unit 20. In FIG. 7, the ion trap 30 is provided inside the mixing chamber 16. In an alternative embodiment the ion trap 30 may also be provided to the filter inlet channel 36 between the mixing chamber 16 and the filter unit 20.

The filter unit 20 comprises a housing 26 inside which a filter 22 is arranged. The housing 20 comprises or is formed as a faraday cage for electrically separating the filter unit 20 from the other parts of the apparatus 1, and especially from the ionization chamber 6, electrical charging element 8, ion trap and the mixing chamber 16. The filter unit 20 further comprises an electrical insulator 23 inside the housing 20. The filter 22 is embedded inside the insulator 23 for further electrically insulating the filter 22 from the other parts of the apparatus 1. The filter 22 may be any kind of conventional filter, such as carbon filter or HEPA filter or some other kind of filter. The structure of the filter unit 20 is arranged such that the filter 22 may be removed from the filter unit 20 and replaced or changed to a new filter 22.

The electrically charged particles of the mixed sample aerosol are filtered and removed from the mixed sample aerosol in the filter 22. During the filtration with the filter 22 the electrically charged particles are deposited to the filter 22 and accumulate to the filter 22.

As the electrically charged particles are deposited to the filter 22 they generate electrical current to the filter 22. The filter unit 20 therefore further comprises electrical measurement element 24 connected to the filter 22. The electrical measurement element 24 is arranged to measure the electrical current produced by the electrically charged particles in the filter 22 as they are deposited to the filter 22. The electrical measurement element 22 provides an output signal based on the measurement results of the electrical current measurements from the filter 22. The output signal may be transmitted to a process unit (not shown) for further analysis. The electrical measurement element 24 may comprise an electrometer or the like measuring device.

The ion trap has to be arranged upstream of or before the filter unit 20 such that the free ions present invention mixed sample aerosol do not affect the particle measurement based on the measuring the electrical current carried by the electrically charged particles.

In the filter unit 20 the electrically charged particles are filtered from the mixed sample aerosol and a filtered mixed sample aerosol flow is discharged from the filter unit 20.

Downstream of the filter unit 20 is provided a pump 28 or other kind of suction device. The pump 28 is arranged in fluid communication with the filter unit 20 and arranged downstream of the filter unit 20. The pump 28 is arranged to generate flow of at least sample aerosol, mixed sample aerosol and filtered mixed sample aerosol through the apparatus 1. The pump 28 may also be arranged to generate flow of the clean gas and ionized clean gas into or in the apparatus 1.

The pump 28 is connected to the filter unit 20 with a filter output channel 38 extending between the filter unit 20 and the pump 28 for passing the filtered mixed sample aerosol from the filter unit 20 to the pump 28. The filtered mixed sample aerosol is discharged from the pump 28 and from the apparatus 1 via discharge channel 40. The filtered mixed sample aerosol may be discharged via the discharge channel 40 out of the apparatus 1 to environment or back to the space from where it was taken.

As shown in FIG. 7 the discharge channel 40 discharges the filtered mixed sample aerosol out from the apparatus 1. The discharge channel 40 comprises in this embodiment of the invention a clean gas intake 42 for feeding filtered mixed sample aerosol as a clean gas toward the ionization chamber 6. The clean gas intake 42 provides an opening for the clean gas channel 32. The embodiment of the invention shown in FIG. 7 does not have any additional clean gas filters in the clean gas channel 32 but instead the additional clean gas filter is arranged in connection with the ionization chamber and the clean gas inlet 4 such that the clean gas supplied from the clean gas inlet 4 is fed through the additional clean gas filter 46 before being ionized in the ionization chamber 6.

FIG. 8 shows the apparatus 1 shown in FIG. 7 when at least partly disassembled. The apparatus 1 comprises an ionization chamber 6 having a charging element 8 arranged in the ionization chamber 6 for charging the clean gas into ionized clean gas, and an ionized gas outlet 12 for discharging the ionized clean gas from the ionization chamber 6. The electrical charging element 8 is connected to charging voltage source 10 which however is not shown in FIG. 8 for providing charging voltage to the electrical charging element 8. The charging voltage source 10 may be any kind voltage source, such as high voltage source. The apparatus 1 further comprises a mixing chamber 16 in which the ionized clean gas flow and the particle containing sample aerosol flow meet each other and are mixed with each other for providing a mixed sample flow. The mixing chamber 16 is defined by mixing chamber walls 31. In the mixing chamber 16 the ionized clean gas flow and the sample aerosol flow collide and mix with each other such that the ionized clean gas electrically charges the particles of the sample aerosol providing a mixed sample aerosol comprising electrically charged particles. In the embodiment shown in FIG. 8 the mixing chamber 16 and the ionization chamber 6 are detached from the filter unit 20. The ionization chamber 6 is detached from the filter unit 20 as one component comprising the charging element 8 and the clean gas filter 46 arranged inside the ionization chamber 6.

The apparatus 1 has a stacked structure such that the ionization chamber 6 is arranged within the mixing chamber 16 forming a nested structure with said mixing chamber 16. As can be seen from FIG. 8 in the preferred embodiment of the invention the ionization chamber 6 and the mixing chamber 16 are arranged such that the ionized gas outlet 12 and the sample inlet 14 are arranged opposite to each other providing a counter current flow of the ionized clean gas and the sample aerosol inside the mixing chamber 16. This provides a compact structure for the apparatus 1 and also efficient mixing of the ionized clean gas and the sample aerosol in the mixing chamber 16. The ionization chamber 6 may comprise a clean gas filter 46 arranged inside the ionization chamber 6 for further cleaning the clean gas separated from the discharge channel 40 and transferred through the clean gas channel 32 to the clean gas inlet 4.

The FIG. 8 shows one embodiment of the invention in which he mixing chamber 16 is connected to the filter unit 20 with a releasable connection as well as the ionization chamber 6 is connected to the filter unit 20 with a releasable connection. The releasable connection is preferably arranged through a mechanical structure between the housing 26 and the mixing chamber 16 and/or between the housing 26 and the ionization chamber 6. The mechanical structure is for example a flange connection or a threaded end mounting or other mechanical structure that is easily openable and further closable.

FIG. 9 shows another embodiment of the invention of the apparatus 1 having a stacked structure such that the ionization chamber 6 is arranged within the mixing chamber 16 forming a nested structure with said mixing chamber 16 which the embodiment shown in FIG. 9 can be combined with the teaching in FIG. 8 in which the mixing chamber 16 and ionization chamber 16 are releasable connected to the filter unit 20 or the embodiment of FIG. 9 can be combined with the ionization chamber 6 is arranged within the mixing chamber 16 forming a nested structure that is not releasable connected to the filter unit.

The housing 26 of the filter unit 20 in FIG. 9 comprises an openable cover for removing the filter from the housing 26 or placing the filter 22 to the housing 26. The openable cover is arranged to the housing 26 such that the filter 22 is removable from the housing by opening the openable cover. The openable cover is preferably arranged in the side of the ionization chamber 6 but it may alternatively be arranged to the front side of the apparatus 1 such that the nested structure of the ionization chamber 6 and the mixing chamber 16 are not moved when opening the openable cover.

As shown in FIG. 9 the housing 26 of the filter unit 20 comprises a hinge 48 arranged to open the openable cover. Another example of the invention is that the openable cover is detachable from the rest of the housing 26. This means that the openable cover can be disconnected from the rest of the housing 26 and put back again. The hinged version of the op enable cover is more preferable because then all the connections in the apparatus for electricity can stay untouched. In the detachable version of the openable cover the housing 26 and/or the openable cover comprises at least one fixed contact member to provide a contact point between the housing and the openable cover.

As shown in all the FIGS. 1 to 3 the mixing chamber 16, the filter unit 20 and the pump 28 are arranged in line such that the flow direction of the sample aerosol coming from the sample inlet 14 and further the mixed sample aerosol formed in the mixing chamber 16 is substantially parallel all the way through the apparatus 1. Preferably the ionization chamber 6 together with the ion trap 30 is also in line with the mixing chamber 16 and the pump 28.

It will be obvious to a person skilled in the art that, as the technology advances, the inventive concept can be implemented in various ways. The invention and its embodiments are not limited to the examples described above but may vary within the scope of the claims.

According to the above mentioned and FIGS. 7, 8 and 9 the apparatus 1 comprises: an ionization chamber 6 comprising a clean gas inlet 4 for feeding clean gas into the ionization chamber 6, a charging element 8 arranged in the ionization chamber 6 for charging the clean gas into ionized clean gas, and an ionized gas outlet 12 for discharging the ionized clean gas from the ionization chamber 6; a mixing chamber 16 comprising a sample inlet 14 for feeding sample aerosol into the mixing chamber 16, said mixing chamber 16 is in a fluid communication with the ionization chamber 6 for feeding ionized clean gas from the ionization chamber 6 into the mixing chamber 16, and a mixing chamber outlet 18 for discharging mixed sample aerosol formed in the mixing chamber 16 by mixing ionized clean gas and sample aerosol, said mixed sample aerosol comprising electrically charged particles; an ion trap 30 for removing ions not attached to particles from the mixed sample aerosol; a filter unit 20 for filtering electrically charged particles from the mixed sample aerosol for forming filtered mixed sample aerosol, said filter unit 20 comprising a filter 22 and a housing 26, said filter unit 20 is in fluid communication with the mixing chamber 16 and arranged downstream of the mixing chamber 16; a pump 28 for generating flow of clean gas, ionized clean gas, sample aerosol, mixed sample aerosol and filtered mixed sample aerosol, said pump 28 is in fluid communication with the filter unit 20 and arranged downstream of the filter unit 20; and a discharge channel 40 connected to the pump 28 for discharging filtered mixed sample aerosol from the apparatus 1; the apparatus 1 has a stacked structure such that the ionization chamber 6 is arranged within the mixing chamber 16 forming a nested structure with said mixing chamber 16.

The ionization chamber 6 and the mixing chamber 16 may be arranged such that the ionized gas outlet 12 and the sample inlet 14 are arranged opposite to each other providing a counter current flow of the ionized clean gas and the sample aerosol inside the mixing chamber 16.

The ionization chamber 6 may comprise a clean gas filter 46 arranged inside the ionization chamber 6.

The mixing chamber 16 may be connected to the filter unit 20 with a releasable connection.

The releasable connection may be arranged through a mechanical structure between the housing 26 and the mixing chamber 16.

The ionization chamber 6 may be connected to the filter unit 20 with a releasable connection. The releasable connection may be arranged through a mechanical structure between the housing 26 and the ionization chamber 6.

The housing 26 of the filter unit 20 comprises an openable cover for removing the filter from the housing 26 or placing the filter 22 to the housing 26. The housing 26 may comprise a hinge 48 arranged to open the openable cover. The openable cover is detachable from the rest of the housing 26. The housing 26 and/or the openable cover may comprise at least one fixed contact member to provide a contact point between the housing and the openable cover.

The mixing chamber 16, the filter unit 20 and the pump 28 are arranged in line such for providing a substantially parallel flow direction of the sample aerosol coming from the sample inlet 14 and further the mixed sample aerosol formed in the mixing chamber 16.

It will be obvious to a person skilled in the art that, as the technology advances, the inventive concept can be implemented in various ways. The invention and its embodiments are not limited to the examples described above but may vary within the scope of the claims.

The invention claimed is:

1. An apparatus for particle measurement, the apparatus comprising:

a mixing chamber comprising a sample inlet provided to the mixing chamber for feeding sample aerosol containing particles into the mixing chamber, an ionized gas outlet for feeding ionized clean gas into the mixing chamber, and a mixing chamber outlet for discharging mixed sample aerosol formed in the mixing chamber by mixing ionized clean gas and sample aerosol, said mixed sample aerosol comprising electrically charged particles generated by the ionized clean gas;

a sample channel connected to the sample inlet for supplying sample aerosol into the mixing chamber via the sample inlet, the sample channel extending in a first supply direction;

a sample supply connection arranged to supply sample aerosol to the sample channel;

a sample supply channel connected to the sample supply connection in a second supply direction perpendicular, inclined or transverse in an angle to the first supply direction, the sample supply channel arranged to supply sample aerosol to the sample channel via the sample supply connection;

an ion trap for removing free ions not attached to particles from the mixed sample aerosol; and an electrical measurement element arranged to measure electrical current carried by the electrically charged particles, the sample supply connection being arranged to supply the sample aerosol from the sample supply channel to the sample channel as a swirling sample aerosol flow, whereby the sample supply connection is a tangential connection of the sample supply channel to the sample channel in relation to the first supply direction for providing the swirling aerosol flow around the first central axis along the sample channel; or the sample channel has a first central axis extending in the first supply direction and circular or elliptical cross-section provided by sample channel side wall, and that the sample supply connection is a tangential connection of the sample supply channel to the sample channel side wall in relation to the first central axis for providing the swirling aerosol flow around the first central axis along the sample channel; or the sample supply connection comprises one or more guide vanes provided inside or to inner walls of the sample supply connection for providing the swirling sample aerosol flow to the sample channel.

2. An apparatus according to claim 1, wherein the second supply direction is transverse in an angle to the first supply direction; or the second supply direction is inclined to the first supply direction; or the second supply direction is perpendicular to the first supply direction.

3. An apparatus according to claim 1, wherein the sample supply connection comprises a sample supply chamber arranged between the sample supply channel and the sample channel and arranged to receive the sample aerosol in the second supply direction from the sample supply channel and to supply the sample aerosol to the sample channel extending in the first supply direction, and that the sample supply channel is arranged to supply the sample aerosol from the sample supply channel to the sample supply connection tangentially in relation to the first supply direction for proving the swirling sample aerosol flow to the sample channel.

4. An apparatus according to claim 3, wherein the sample supply chamber has a second central axis extending in the first supply direction, the sample supply chamber being arranged to provide the swirling sample aerosol flow around the second central axis and to supply the sample aerosol to the sample channel.

5. An apparatus according to claim 3, wherein the sample supply chamber is a tubular or cylindrical sample supply chamber having the second central axis extending in the first supply direction and a circular or elliptical cross-section, or circular or elliptical sample supply chamber side wall, the swirling aerosol flow being arranged to flow around the second central axis.

6. An apparatus according to claim 3 5, wherein:

the sample supply channel is connected tangentially to the sample supply chamber for supplying the sample aerosol to the sample supply chamber tangentially; or the sample supply channel is connected tangentially to the circular or elliptical sample supply chamber side wall of the sample supply chamber for supplying the sample aerosol to the sample supply chamber tangentially.

7. An apparatus according to claim 3, wherein the sample supply channel is connected to the sample supply chamber in the second supply direction, the second supply direction being:

transverse in an angle to the first supply direction; or inclined to the first supply direction; or perpendicular to the first supply direction.

8. An apparatus according to claim 3, wherein the sample supply chamber is a separate chamber provided between the sample supply channel and the sample channel, or that the upper end of the sample channel forms the sample supply chamber.

9. An apparatus according to claim 1, wherein the first supply direction is vertical direction and the second supply direction is horizontal direction, or that the first supply direction is horizontal direction and the second supply direction is vertical direction.

10. An apparatus according to claim 1, wherein the apparatus further comprises one or more of the following:

an ionization chamber comprising a clean gas inlet for feeding clean gas into the ionization chamber, a charging element arranged in the ionization chamber for charging the clean gas into ionized clean gas, and the ionized gas outlet for discharging the ionized clean gas from the ionization chamber to the mixing chamber, the ionizing chamber being in a fluid communication with the mixing chamber for feeding ionized clean gas from the ionization chamber into the mixing chamber;

a filter unit arranged to filter electrically charged particles from the mixed sample aerosol for forming filtered mixed sample aerosol, said filter unit, said filter unit is in fluid communication with the mixing chamber and arranged downstream of the mixing chamber, the electrical measurement element being connected to the filter unit for measure electrical current carried by the electrically charged particles and deposited to the filter unit;

a pump for generating flow of clean gas, ionized clean gas, sample aerosol, mixed sample aerosol and filtered mixed sample aerosol, said pump is in fluid communication with the filter unit arranged downstream of the filter unit; and a discharge channel connected to the pump for discharging filtered mixed sample aerosol from the apparatus.

11. An apparatus according to claim 1, wherein the apparatus further comprises a preliminary separation device connected to the sample supply channel upstream of the sample supply connection, the preliminary separation device being arranged adjacent to the mixing chamber.

12. A method for particle measurement with an apparatus for particles measurement, the method comprising:

feeding sample aerosol containing particles into a mixing chamber along a sample channel and via a sample inlet provided to the mixing chamber, the sample channel extending in a first supply direction;

feeding ionized clean gas into the mixing chamber via an ionized gas outlet;

mixing ionized clean gas and sample aerosol in the mixing chamber for electrically charging particles of the sample aerosol and providing mixed sample aerosol comprising electrically charged particles generated by the ionized clean gas;

removing free ions not attached to particles from the mixed sample aerosol;

measuring electric current carried by the electrically charged particles; and supplying sample aerosol to the sample channel via a sample supply connection from a second supply direction perpendicular, inclined or transverse in an angle to the first supply direction such that a swirling sample aerosol flow is generated to the sample channel in relation to the first supply direction, wherein the sample aerosol is supplied tangentially to the sample supply connection from the second supply direction transverse to the first supply direction for providing the swirling sample aerosol flow to the sample channel in relation to the first supply direction or the swirling sample aerosol flow to the sample channel is provided by using guide vanes provided inside or to inner walls of the sample supply connection.

* * * * *